US012643863B2

(12) United States Patent
Wulff et al.

(10) Patent No.: US 12,643,863 B2
(45) Date of Patent: Jun. 2, 2026

(54) DIAZIRINE-BASED MOLECULES AND USES THEREOF

(71) Applicant: XLYNX MATERIALS INC., Sidney (CA)

(72) Inventors: Jeremy E Wulff, Victoria (CA); Peter G Berrang, Sidney (CA); Mathieu L Lepage, L'Huisserie (FR); Chakravarthi Simhadri, Victoria (CA)

( * ) Notice: Subject to any disclaimer, the term of this patent is extended or adjusted under 35 U.S.C. 154(b) by 1158 days.

(21) Appl. No.: 17/606,649

(22) PCT Filed: Feb. 28, 2020

(86) PCT No.: PCT/CA2020/050278
§ 371 (c)(1),
(2) Date: Oct. 26, 2021

(87) PCT Pub. No.: WO2020/215144
PCT Pub. Date: Oct. 29, 2020

(65) Prior Publication Data

US 2022/0281820 A1 Sep. 8, 2022

Related U.S. Application Data

(60) Provisional application No. 62/839,062, filed on Apr. 26, 2019.

(51) Int. Cl.
*C07D 229/02* (2006.01)
*C07D 401/14* (2006.01)
*C08J 3/24* (2006.01)

(52) U.S. Cl.
CPC ......... *C07D 229/02* (2013.01); *C07D 401/14* (2013.01); *C08J 3/24* (2013.01); *C08J 2323/06* (2013.01)

(58) Field of Classification Search
CPC .. C07D 229/02; C07D 401/14; C07D 213/54; C07D 213/78; C07D 213/80; C07D 401/04; C08J 3/24; C08J 2323/06
See application file for complete search history.

(56) References Cited

U.S. PATENT DOCUMENTS

2003/0113279 A1* 6/2003 Vic ........................ A61Q 17/04 536/123
2016/0083352 A1 3/2016 Burgoon et al.
2017/0279048 A1* 9/2017 Rhodes ................. C08F 132/08
2018/0175303 A1* 6/2018 Kim ........................ C01B 25/02
2018/0186747 A1 7/2018 Burgoon et al.

FOREIGN PATENT DOCUMENTS

WO 2013012961 A2 1/2013
WO 2017/165478 A1 9/2017
WO 2019/050479 A1 3/2019

OTHER PUBLICATIONS

H. Mehenni et al., "Synthesis and Application of New Photocrosslinkers for Poly(ethylene glycol)", Australian Journal of Chemistry, vol. 65(2), 193-201, 2012, See International Search.
A. Blencowe et al., "A carbene insertion approach to functionalised poly(ethylene oxide)-based gels", Reactive & Functional Polymers, vol. 68(4), 868-875, 2008, See International Search.
A. Welle et al., "Tri- and tetravalent photoactivable cross-linking agents", Synthesis, vol. 44(14), 2249-2254, 2012, See International Search.

* cited by examiner

*Primary Examiner* — Jessica M Roswell

(57) ABSTRACT

A family of novel diazirine-based molecules as well as methods of manufacture and uses thereof are disclosed. These compounds allow non-functionalized polymers, such as polyolefins, to crosslink via C—H insertion. Such a C—H insertion process is useful, for example, for forming protective topical coatings on low surface energy films, for the covalent adhesive bonding of such films, or for creating rigid 3-dimensional polymeric structures by in-situ doping and activation of the crosslinker. The crosslinkers can be activated thermally, by UV radiation or by an electric potential.

2 Claims, 9 Drawing Sheets

| Compound | CL-PH | CL-PY | CL-HF2PH |
|---|---|---|---|
| Structure |  |  |  |
| n = | 3 | 4 | 4 |
| Enthalpy (J/g) | 1242 ± 92 | 1395 ± 75 | 696 ± 24 |
| Enthalpy (kJ/mol) | 365 ± 27 | 412 ± 22 | 362 ± 13 |
| $E_{diazirine}$ (kJ/mol) | 183 ± 14 | 206 ± 11 | 181 ± 7 |
| Onset temperature (°C) | 112.9 ± 2.1 | 106.5 ± 1.1 | 113.1 ± 0.2 |
| Shock sensitivity | LIKELY (+0.09) | LIKELY (+0.17) | Not likely (-0.16) |
| Explosive propagation | LIKELY (+0.06) | LIKELY (+0.13) | Not likely (-0.19) |

DIAZIRINE-BASED MOLECULES AND USES THEREOF

FIELD

Crosslinking of polymers, particularly of non-functionalized polymers.

BACKGROUND

Crosslinking of polymers increases mechanical strength and thermal stability, reduces material creep at high temperatures, provides resistance to electrical discharge, and offers increased stability to solvents and stress cracking. Moderate levels of crosslinking are known to be tolerated in many materials without the deleterious introduction of brittleness, and crosslinked polymers are already extensively used in everything from construction equipment to medical devices. However, the creation of interchain crosslinks generally requires that functional groups are already present within the polymer structure.

In cases where such functionality is absent, high energy processes (e.g. gamma-irradiation or introduction of free radicals) must be used to abstract hydrogen atoms. Such processes are expensive, non-tunable (tunability is the ability to rationally modify the properties of the final material by altering the properties and concentration of the crosslinker, or by altering the cross-linking conditions in a systematic way) and do not work for many industrially-important polymers (e.g. polypropylene) due to competing chain-fragmentation processes.

Addition of crosslinks to polymeric materials confers several important advantages to the final product. Impact resistance and tensile strength are increased, and material creep is vastly de-creased. By fundamentally transforming a thermoplastic material into a thermoset, high temperature performance is greatly enhanced, and unwanted shrinkage at low temperature is reduced. Depending upon the nature and density of the chemical crosslinks, such materials often acquire shape memory, meaning that a deformed object will return to its original shape with the application of heat. These types of mechanical properties are required for many commercially important products.

Crosslinked materials also have increased resistance to solvents and electrical discharge, as well as to biological and chemical degradation. This is advantageous in applications where chemical-, biological- or electrically-promoted corrosion must be guarded against. Crosslinked polyethylene ("PEX"), for example, is used extensively for medical devices, as insulation for electrical wires, and for pipes used to transport corrosive liquids.

One potential disadvantage to crosslinking lies with an increase in brittleness. Because the polymer chains are no longer free to slip across each other, high-impact challenges can result in catastrophic material fracture. However, it is known in the art that, so long as the density of crosslinks is well controlled, brittleness can be avoided. Crosslinked polyethylene tubing, for example, typically has a crosslink density of 65-89%, while applications requiring greater flexibility have lower crosslink densities.

Crosslinks can be established in polymers in a number of ways. A common method for establishing a defined percentage of crosslinks involves first synthesizing a copolymer wherein one of the monomer constituents incorporates a linkable fragment. Such methods are not preferred industrially, as the monomer components are often rather expensive or difficult to synthesize. Further, the heavily functionalized copolymer often lacks the high strength or chemical resistance required for industrial applications.

Another strategy to achieve crosslinking involves the use of a monomer which has two functional groups—one to participate in the initial polymerization, and another to participate in subsequent crosslinking events. For example, in the industrially important thermoset material polydicyclopentadiene, one alkene in the monomer participates in the principal polymerization event, while a second alkene is principally responsible for crosslinking.

Unfortunately, neither of the above strategies is appropriate when one needs to crosslink all existing polymer material that has desirable properties (mechanical strength, ease of production, low cost, durability, etc.) but which lacks functionality within its chemical structure. This includes many extremely important industrial materials. For example, polyethylene (annual global production ~80 million tonnes), and polypropylene (~55 million tonnes) are arguably the most important petrochemical-derived polymers on the planet, but do not easily lend them-selves to chemical crosslinking. Similarly, biomass-derived polymers like polylactic acid and important biodegradable polymers like polycaprolactone often lack any crosslinkable functional groups, even though they contain some measure of functionality within their linear chains.

Existing methods for crosslinking unreactive polymers have a number of disadvantages. For example, crosslinked polyethylene can be produced by peroxide-initiated radical crosslinking. In this method, peroxide additives (e.g. dicumyl peroxide) are physically combined with polyethylene through an extrusion process. The resulting peroxide-impregnated polymer is then heated at high temperatures (typically 200-250° C.) to initiate the formation of radicals, which in turn results in abstraction of hydrogen atoms and eventual crosslinking. The key problem with prior art radical-based crosslinking methods is the need to break a very strong C—H bond, the strength for which is about 401 kJ/mol for the 2° C.—H in polyethylene, and about 389 kJ/mol for the 3° C.—H in polypropylene. Fundamentally, the need to generate such high-energy species as alkyl radicals means that little-to-no control is possible using crosslinking methods known in the prior art. Moreover, the carbon-centered radicals produced following cleavage of these strong C—H bonds are highly reactive and can undergo fragmentation (β-scission) reactions at rates that are competitive with crosslinking. This results in breakage of the polymer chains, and therefore reduces material strength.

Crosslinked polyethylene can also be produced by treatment with either gamma-rays or electron beams. As with radical crosslinking methods, these processes proceed via an initial cleavage of strong C—H bonds, and so suffer many of the disadvantages outlined above. The polymers produced using gamma-rays may, in some cases, have superior mechanical properties to those generated by peroxide-initiated methods, but the substantial costs associated with this process limits its use to the production of small-scale medical devices.

Both of the above methods (as well as related processes like silanization) generate intermediate radicals which can undergo β-scission and other undesirable side-reactions. β-Scission is reversible, and so tends not to be a limitation for crosslinked polyethylene (especially in high-density polyethylene); since the polymer chains are held close together, the products of radical fragmentation simply recombine to give the original secondary radical intermediate. For poly-propylene, however, these types of processes are much more problematic.

A third problem with radical crosslinking is that the intermediates resulting from β-scission can recombine in a regiochemically different manner, ultimately leading to unexpected branching of the polymer structure. This can lead to a loss of crystallinity, and at the very least is hard to predict and control.

The crosslinking processes summarized above are not particularly tunable, beyond simply empirically controlling for total crosslink density. There is no provision for controlling the length or rigidity of the crosslink structure (which could be extremely useful in mitigating brittleness at high crosslink densities), nor is there any possibility to enhance the functionality of an existing polymer through these methods.

Indeed, given that isotactic polypropylene has higher mechanical strength than polyethylene (not to mention a higher melting point and better heat resistance), it is quite surprising that there is essentially no good crosslinking method available for polypropylene. This speaks not only to the significant limitations associated with radical-based crosslinking, but also suggests a significant untapped market for an eventual crosslinked polypropylene product.

Methods are known in the art for crosslinking polymers using diazirines. Burgoon (US patent applications 20160083352 and 20180186747) discloses a family of diazirines useful as photo-crosslinkers in the preparation of photoimageable compositions for film coating microelectronic or optoelectronic devices.

In general, the methods known in the art for application of diazirine-based crosslinkers all employ polymers that have existing functionality within their chemical structure beyond simple C—C and C—H bonds. The presence of such functionality either facilitates crosslinking or else lowers C—H bond strength (as is the case, for example, with polyether materials such as polyethylene oxide). Such functional polymers are generally intended for use in electronics applications (OLEDs, etc.). There is no teaching in the art that compounds such as those of Formula I or II can be used for crosslinking unfunctionalized polymers such as polyethylene or polypropylene.

SUMMARY

To address this core limitation of the prior art, we have designed a novel class of diazirine molecules (which includes bis-, tris- and tetrakis-diazirines) as shown in Formula I, below:

Formula I

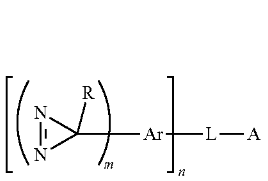

wherein:

R, in each instance, is independently selected from the group consisting of alkyl and cycloalkyl;

Ar is selected from the group consisting of null and aryl;

L is a linker moiety selected from the group consisting of null, alkylene, and cycloalkylene;

A is a cargo moiety, which may be absent;

m is an integer from 1 to 4; and n is an integer from 1 to 4;

with the provisos that Ar and L cannot both be null, m and n cannot both be 1 and that the compound is not 1,3-bis(3-(trifluoromethyl)-3H-diazirin-3-yl)benzene.

Compounds of Formula I are useful as crosslinkers, and have advantages over methods of the art. They have a low barrier to C—H insertion, and so allow for the controllable crosslinking of essentially any polymer containing C—H bonds. Moreover, crosslinkers of Formula I permit tunability within the chemical structure of the crosslink itself. They are particularly useful for the crosslinking of non-functionalized polymers.

Also disclosed is the use of compounds of Formula II as crosslinkers:

Formula II

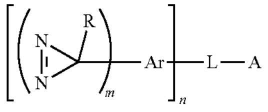

wherein:

R, in each instance, is independently selected from the group consisting of alkyl and cycloalkyl;

Ar is selected from the group consisting of null and aryl;

L is a linker moiety selected from the group consisting of null, alkylene, cycloalkylene, ether, ketone, amide, ester and aryl;

A is a cargo moiety, which may be absent;

m is an integer from 1 to 4; and n is an integer from 1 to 4;

with the provisos that Ar and L cannot both be null, m and n cannot both be 1.

Compounds of Formula II are useful as crosslinkers, and are particularly useful for the crosslinking of non-functionalized polymers.

BRIEF DESCRIPTION OF THE DRAWINGS

These and other features will become more apparent from the following description in which reference is made to the appended drawings, the drawings are for the purpose of illustration only and are not intended to be in any way limiting, wherein.

insoluble fraction from paraffin wax cross-linked with 200 w % CL-HF2PH (the picture was taken several days after the swelling: the solvent had evaporated, and the resin had de-swollen).

Figure 8:
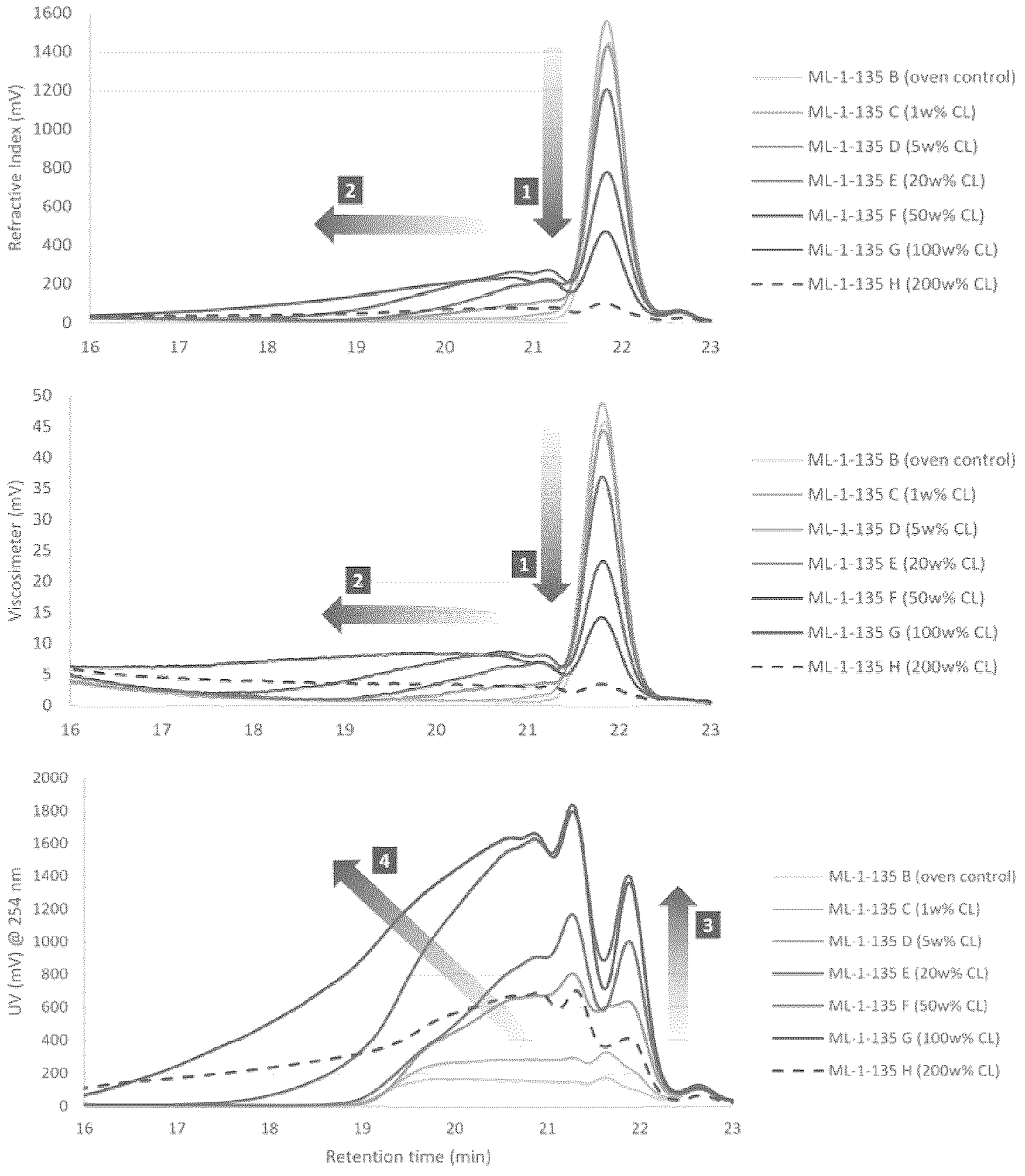

FIG. 8 is a series of stacked gel permeation chromatograms. Traces of paraffin wax were crosslinked with increasing loadings of CL-HF2PH. The more intense the color, the higher the loading of CL-HF2PH. Sample H (200 w % cross-linker added) is displayed as a dashed line. Note: Samples A (room temperature control) and B (oven control) had a similar GPC trace; only sample B trace is displayed here. Arrows 1-4 illustrate changes in molecular weight upon crosslinking.

Figure 9:
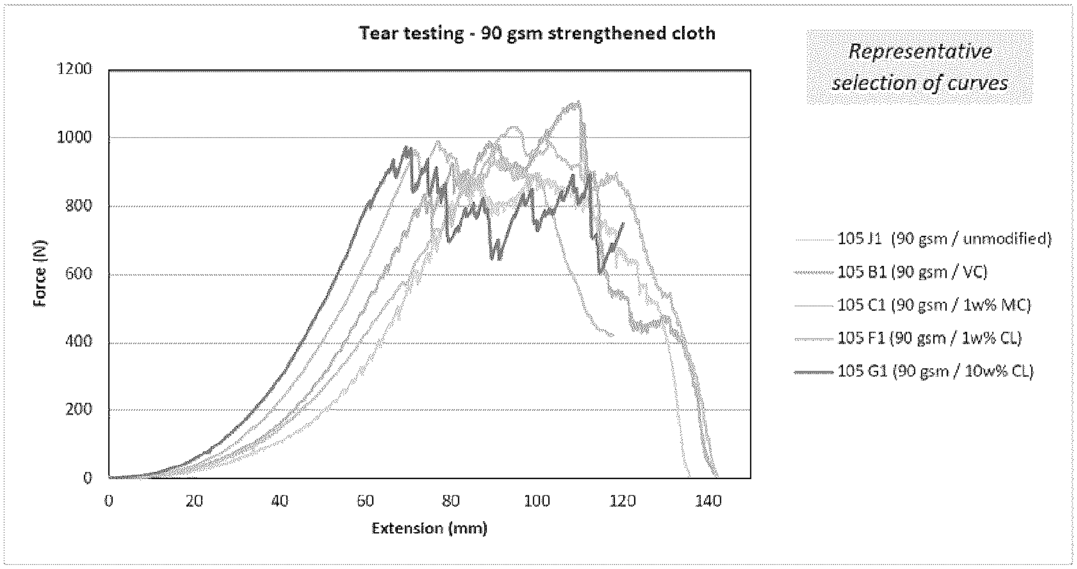

FIG. 9 is a chart of a representative selection of curves for tear testing analysis of 90 g/$m^2$ UHMWPE fabric (unmodified, vehicle control (VC), 1 w % molecular control (MC), 1 w % cross-linked, 10 w % cross-linked).

DETAILED DESCRIPTION

Disclosed are compounds of Formula I:

Formula I

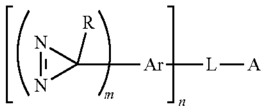

wherein:

R, in each instance, is independently selected from the group consisting of alkyl and cycloalkyl;

Ar is selected from the group consisting of null and aryl;

L is a linker moiety selected from the group consisting of null, alkylene, and cycloalkylene;

A is a cargo moiety, which may be absent;

m is an integer from 1 to 4; and n is an integer from 1 to 4;

with the provisos that Ar and L cannot both be null, m and n cannot both be 1 and that the compound is not 1,3-bis(3-(trifluoromethyl)-3H-diazirin-3-yl)benzene.

The term alkyl, as used herein, refers to alkyl groups having from 1 to 6 carbons, and includes both linear and branched groups. Non-limiting example of such groups includes methyl, ethyl, and isopropyl. Such alkyl groups may be halogenated. Non-limiting examples of halogenated alkyl groups includes fluoromethyl, difluoromethyl and trifluoromethyl. Preferably, R is a $CF_3$ group.

The term cycloalkyl, as used herein, refers to cycloalkyl groups having from 1 to 6 carbons, and includes cyclopropyl, cyclobutyl, cyclopentyl, cyclohexyl and the like. Such cycloalkyl groups may be halogenated. Non-limiting example of such groups include cyclopropyl and perfluorocyclopropyl.

The term aryl, as used herein, encompasses monocyclic and polycyclic aromatic groups such as phenyl, biphenyl, naphthyl, anthracenyl, pyrenyl and the like. It also encompasses heteroaromatic groups such as pyridyl, pyrimidinyl, pyrazinyl, quinolinyl, pteridinyl and the like. Preferably, Ar, when present, is selected from the group consisting of phenyl, perfluorophenyl and pyridyl.

Such aryl groups may be optionally substituted with selected fragments from the group consisting of alkyl, cycloalkyl, halo, hydroxy, alkoxy, amino, alcohols, ethers, carboxylic acids, esters, aldehydes, oximes, hydrazones, amides, thiol, thioethers, sulfinic acids, sulfonic acids, sulfonamides, sulfonyl chlorides, boronic acids, boronic esters, and tetraalkylammonium substituents.

As used herein, the term alkylene refers to divalent, trivalent, or tetravalent alkylene groups having from 1 to 12 carbons, and includes both linear and branched alkylene groups, which may be halogenated.

As used herein, the term cycloalkylene refers to divalent, trivalent, or tetravalent cycloalkylene groups having from 1 to 12 carbons, which may be halogenated.

Preferred alkylene groups have from 1 to 8 carbon atoms, may be linear or branched and, more preferably, be halogenated.

Preferred compounds of Formula I include those in which L is a $C(CF_3)_2$ group or a linear perfluoroalkyl group.

Further, such alkylene groups may be optionally substituted with substituents selected from the group consisting of halo, hydroxy, alkoxy, amino, alcohols, ethers, carboxylic acids, esters, aldehydes, oximes, hydrazones, amides, thiol, thioethers, sulfinic acids, sulfonic acids, sulfonamides, sulfonyl chlorides, boronic acids, boronic esters, and tetraalkylammonium substituents.

The terms cargo and cargo moiety, as used herein, includes moieties which would imbue the resulting crosslinked polymer with specific properties. Non-limiting examples of such groups include dyes, fluorophores, photosensitizers, drug molecules and sensor molecules. The use of such cargo groups allows the preparation of, for example, dyed polyethylene fabric (which is currently challenging to prepare), antibacterial coatings and color-changing impact sensors.

Also disclosed is the use of compounds of Formula II as crosslinkers:

Formula II

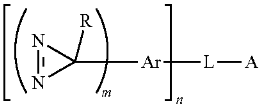

wherein:

R, in each instance, is independently selected from the group consisting of alkyl and cycloalkyl;

Ar is selected from the group consisting of null and aryl;

L is a linker moiety selected from the group consisting of null, alkylene, cycloalkylene, ether, ketone, amide, ester and aryl;

A is a cargo moiety, which may be absent;

m is an integer from 1 to 4; and n is an integer from 1 to 4;

with the provisos that Ar and L cannot both be null, m and n cannot both be 1.

A preferred embodiment of a compound of Formula I is the compound 3,3'-((perfluoropropane-2,2-diyl)bis(4,1-phenylene))bis(3-(trifluoromethyl)-3H-diazirine) (hereinafter referred to as CL-HF2PH). This compound allows for crosslinking between 2 carbons. Other examples of compounds of this type include 3,3'-((perfluorooctane-1,8-diyl)bis(4,1-phenylene))bis(3-(trifluoromethyl)-3H-diazirine), 3,3'-(perfluorooctane-1,8-diyl)bis(3-(trifluoromethyl)-3H-diazirine) and 3,3'-((perfluorooctane-1,8-diyl)bis(2,3,5,6-tetrafluoro-4,1-phenylene))bis(3-(trifluoromethyl)-3H-diazirine).

A further preferred embodiment of a compound of Formula I is 1,3,5-tris(3-(trifluoromethyl)-3H-diazirin-3-yl) benzene. This molecule allows for crosslinking between 3 carbon atoms.

Figure 1:
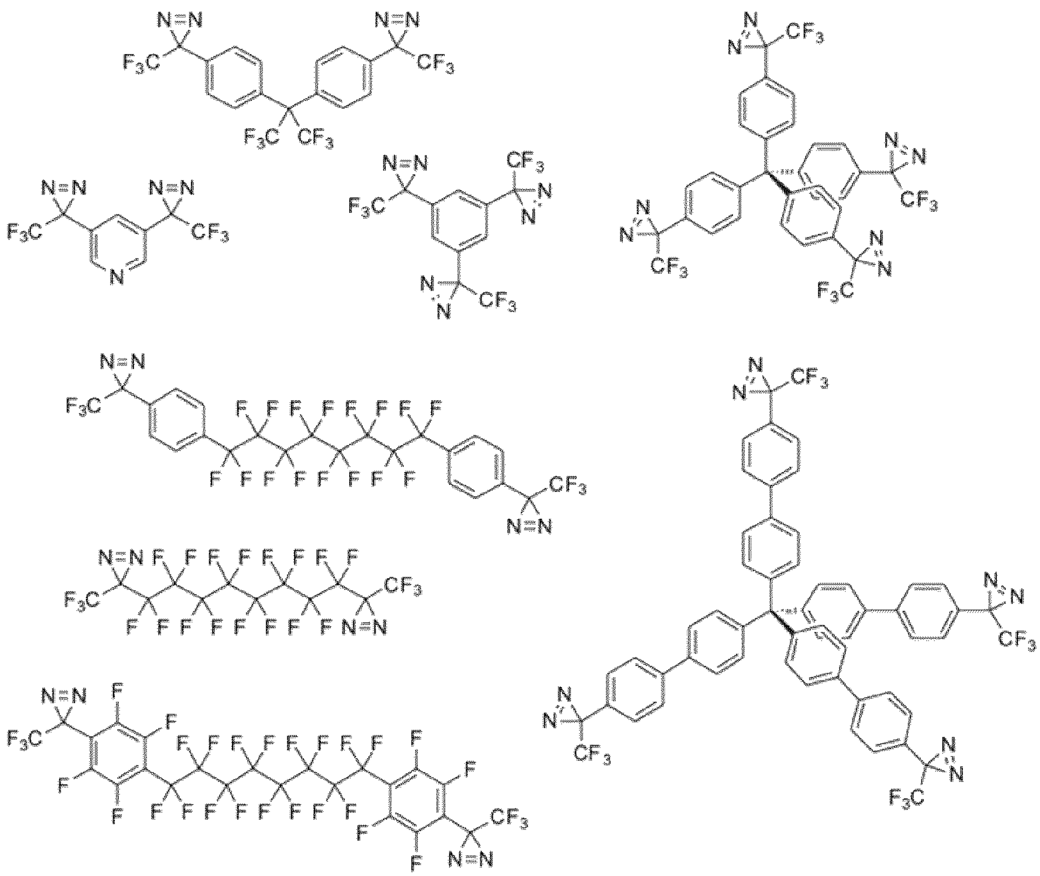
FIG. 1 is an illustration of representative compounds of the invention.

Further preferred embodiments of compounds of Formula I are tetrakis(4-(3-(trifluoromethyl)-3H-diazirin-3-yl)phenyl)methane and tetrakis(4'-(3-(trifluoromethyl)-3H-diazirin-3-yl)-[1,1'-biphenyl]-4-yl)methane. These molecules allow for crosslinking between 4 carbon atoms. Representative compounds of Formula I and Formula II are shown in FIG. 1.

Figure 2:
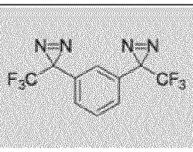
FIG. 2 is a chart showing the thermal properties of CL-PH, CL-PY and CL-HF2PH. Shock sensitivity and explosive propagation are calculated according t Yoshida correlations.
Figure 2:
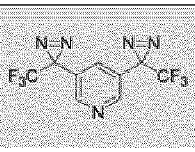
Figure 2:
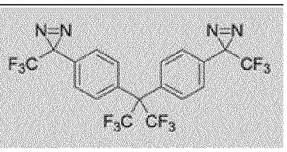
Figure 3:
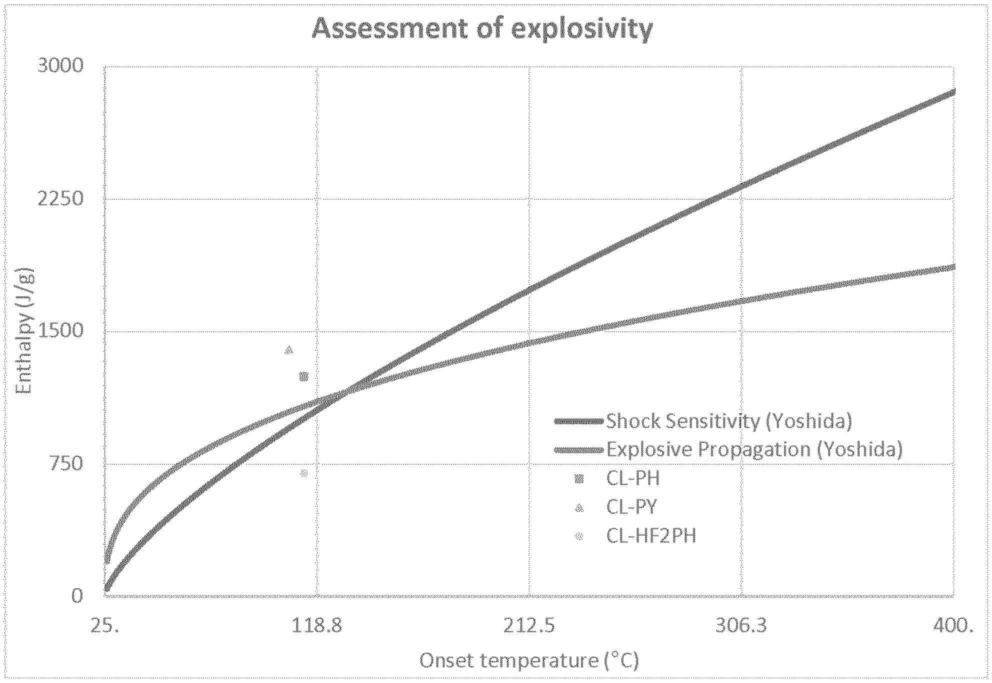
FIG. 3 is a graph showing an assessment of explosivity according to Yoshida correlations (Shock sensitivity and explosive propagation). Compounds are represented by a point of coordinates (Onset temp., Enthalpy), see FIG. 2 for numerical values. Compounds above any of the two curves have the potential to be explosive.

Certain compounds of Formula I and Formula II have a relatively high N:C ratio. Although diazirines have been used for decades without incident, some simple diazirine compounds are known to present explosion hazards. Preferred compounds are those which have properties suitable for use in the processes described herein. Such compounds are not explosive, as determined by DSC data, impact tests, and Yoshida correlation analysis, as shown in FIGS. 2 and 3.

Figure 4:
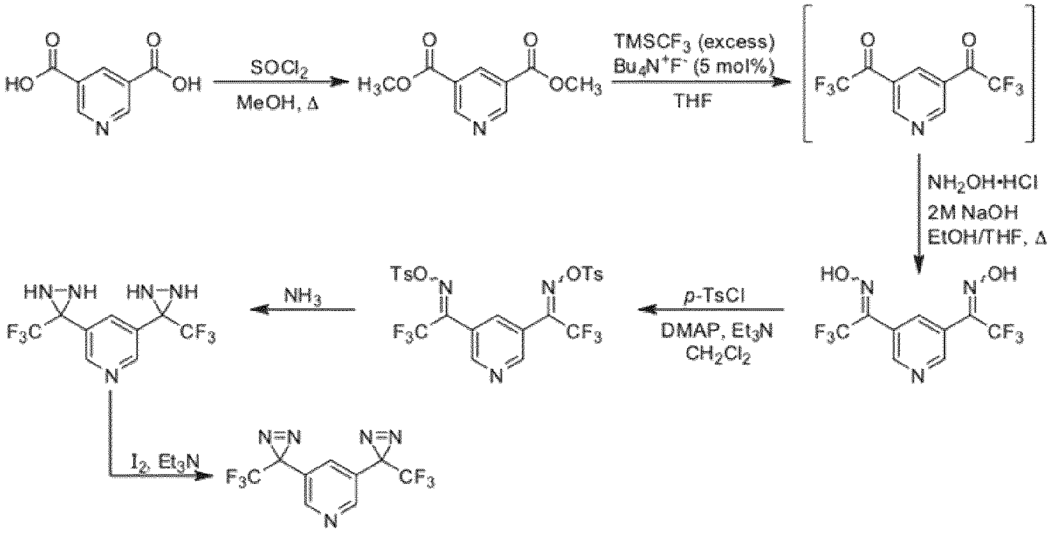
FIG. 4 is an illustration of the synthesis of 3,5-bis(3-(trifluoromethyl)-3H-diazirin-3-yl)pyridine.
Figure 5:
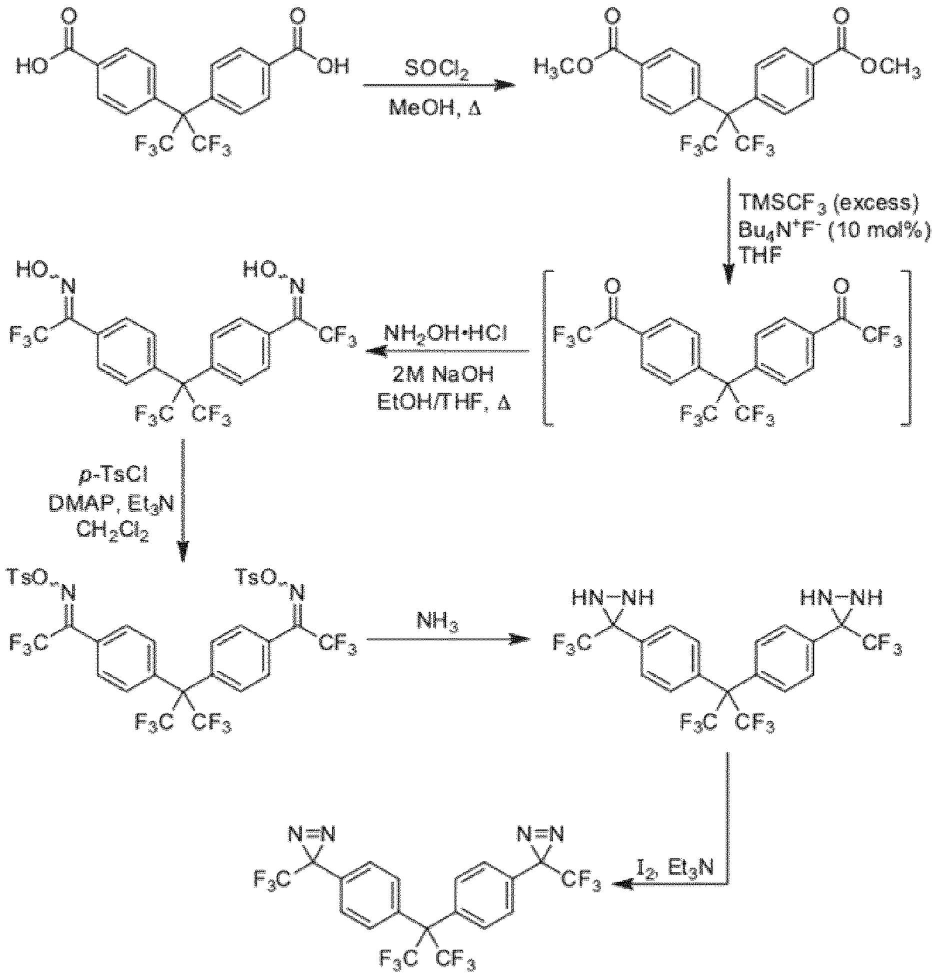
FIG. 5 is an illustration of the synthesis of 3,3'-((perfluoropropane-2,2-diyl)bis(4,1-phenylene))bis(3-(trifluoromethyl)-3H-diazirine).
Figure 6:
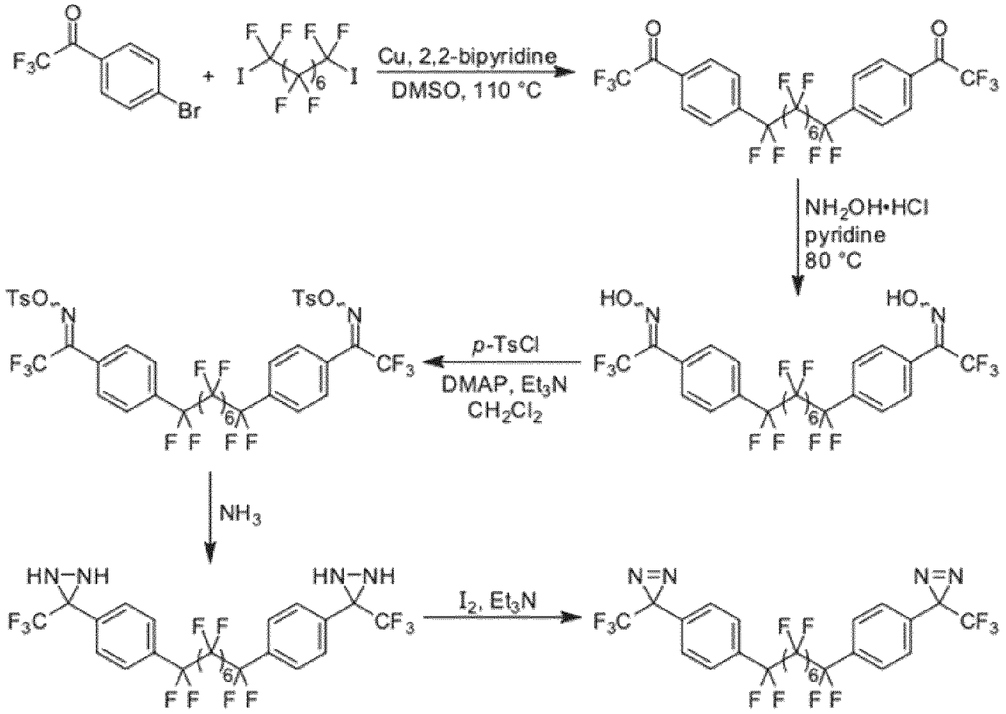
FIG. 6 is an illustration of the synthesis of 3,3'-((perfluorooctane-1,8-diyl)bis(4,1-phenylene))bis(3-(trifluoromethyl)-3H-diazirine).

Compounds of Formula I and Formula II may be prepared using methods known in the art, as described herein. For example, they may be prepared by oxidation of a diaziridine precursor, which may in turn be obtained from the corresponding ketone or other suitable starting reagents. FIGS. 4-6 show a number of approaches to the synthesis of compounds of the invention.

Compounds of Formula I and Formula II are useful as crosslinkers, and have advantages over methods of the art. They have a low barrier to C—H, O—H and N—H insertion, and they allow for the controllable crosslinking of essentially any polymer that contains C—H, O—H or N—H bonds. Moreover, such crosslinkers permit tunability within the chemical structure of the crosslink itself.

Without intending to limit the scope of the invention disclosed herein, it is thought that compounds of Formula I and Formula II work by losing nitrogen to form reactive carbenes, which can then undergo C—H, O—H, or N—H insertion with polymers. This leads to chemical crosslinks. The crosslinking process can increase the material strength of the target polymer, increase the melting temperature, decrease solubility, etc. If two pieces of polymer have a layer of crosslinker in between them, then the crosslinking process results in adhesion. If functional ‘cargo’ is present, then the polymer will acquire new properties (fluorescence, antibacterial activity, conduction, etc.).

Because these C—H insertion steps are nearly barrierless, they allow chemical crosslinking to proceed without β-scission or other fragmentation reactions taking place. Moreover, the crosslinking process can take place with completely unfunctionalized polymers (e.g. polyethylene, polypropylene) as well as with other important polymers that contain functionality but are still not disposed toward crosslinking (e.g. polylactic acid, polycaprolactone). Compounds of Formula I and Formula II also have advantages for polymers which can be crosslinked by more traditional methods (e.g. silicones), but for which there exist limitations with the current crosslinking technologies.

Compounds of Formula I and Formula II can be activated thermally, photochemically, electrically, or through the use of transition metals. Surprisingly, thermal activation appears to be optimal for many applications; for example, in head-to-head crosslinking experiments of unfunctionalized materials (using cyclohexane as a model substrate) thermal activation is superior. By contrast, photochemical activation is the preferred method of activation for prior art methods using diazirines.

With respect to photochemical activation, diazirines can be activated at wavelengths beyond 254 nm, such as 300 or even 350 nm. This is well into the range at which most industrial polymers are optically clear, which means that loss of light to the bulk medium is minimal. Similarly, unwanted photo-degradation of the polymer substrate will be minimized by using these wavelengths, relative to radical-based processes which often require the use of high energy 254 nm light.

In principle, compounds of Formula I and Formula II can be used to crosslink any organic polymer which has C—H or O—H or N—H bonds. Proof-of-concept experiments with polyethylene, polypropylene, polystyrene, polycaprolactone, paraffin (i.e. very short chain polyethylene), polyvinyl alcohol, and silicone bear this out.

Thus, the chemical structure of various polymeric materials can be modified by the topical application or in-situ addition, and activation, of the crosslinkers described herein.

Such chemical modification includes, for example, increasing the polymer’s tensile strength, molecular weight, melting point, “stiffness”, and/or UV resistance and acting as an in-situ foaming agent.

Topical application of the crosslinkers described herein can also increase the polymer’s surface energy, which is a key parameter that expands the commercial uses of such materials. Higher surface energy increases adhesion strength.

Additionally, such topical application can increase the polymer’s surface functionality, thereby enabling improved adhesion of other moieties such as dyes, or metals deposited through chemical vapor deposition protocols.

Topical application of the crosslinkers described herein provides a more permanent, and convenient, method of increasing surface functionality compared to prior art surface treatments such as corona or plasma discharge.

Selected polymers include low surface energy materials having C—H bonds, such as, for example, polyethylene and polypropylene. Materials having O—H or N—H bonds are also applicable.

The format of such polymeric materials includes, for example, premade objects, films, powders, sheets, bare fibres, mesh and ribbons.

Such format materials can be further processed into shapes such as braided lines or ropes, woven and non-woven fabric, alternating orthogonal layers of unidirectional fibres, knitted fabric, laminated films and mesh or web constructs.

Powdered polymeric materials can also be sintered or pressure compacted into various shapes.

For materials comprised of woven or non-woven fibres, or braided lines or ropes, it may be advantageous to use a vacuum or high pressure to facilitate higher penetration of the crosslinker molecule and solvent carrier into such processed material.

The crosslinkers described herein can also be incorporated into the polymer material itself by, for example, by pressure or solvent infusion, where such infusion substantially disperses the crosslinker within the polymer.

Such infusion can be accomplished by dissolving the crosslinker in, for example, a volatile organic solvent such as pentane, (which can be removed prior to activation) at a temperature which does not melt the polymer or cause the crosslinker to activate. Optionally, a vacuum can be first applied to achieve higher crosslinker penetration in materials constructed of braided, woven and non-woven fibres, bare fibres or strands of fibres.

Alternatively, the crosslinker can be pressure infused with or without the use of a solvent carrier.

The addition of a crosslinker can also be accomplished by adding the crosslinker directly into the polymer melt or extrudant. However, such processes are limited to polymers having a melt temperature lower than that of the crosslinker activation temperature, unless such crosslinker is activated non-thermally. Such low melting point polymers include, for example, paraffin, polylactic acid and polycaprolactone.

Various applications of the crosslinkers disclosed herein are described below. These applications are not meant to be comprehensive but, rather, to illustrate some of the chemical modifications made possible by the addition of the disclosed crosslinkers.

Application #1—Surface Energy Modification of Polyolefins by Topical Application The surface energy of polyolefins such as polyethylene and polypropylene is about 24 dynes/cm, which low value makes it difficult to adhesively bond these materials to themselves, or to other materials.

Prior art surface treatments such as corona or plasma discharge, or chemical etching treatments, have been developed to increase surface energy. These treatments randomly disrupt the material surface, and may lead to competitive degradation of the polymer substrate.

The topical treatment of such low surface energy polymers using at least one the crosslinkers disclosed herein provides a new and convenient method to covalently bond low surface energy materials together, or to bond low surface energy materials to other objects.

Alternatively, at least one of the crosslinkers described herein may be used in a surface-treatment protocol to functionalize the surface of a polymer, or to increase its surface energy. Such topical treatment changes the polymer surface functionality in a controlled manner, thereby enabling the surface bonding of moieties such as dyes or metallic vapor-deposited films, including, for example, acrylic and cyanoacrylate-based adhesives.

Application #2—Covalent Bonding of Polyolefin Films

The adhesive or thermal lamination of polyolefin and other polymer films is widely commercially available, especially in the food packaging industry. These packaging film laminates include a variety of high tensile strength biaxially oriented films.

However, bonding polyolefin films, especially PP (polypropylene) films, and BOPP (biaxially oriented polypropylene) is problematic, as peel strength (i.e. film bonding adhesion) requires prior surface treatment and is limited in peel strength between laminated films.

Also, polyethylene films, such as HDPE (high density polyethylene) and UHMWPE (ultra high molecular weight polyethylene) are difficult to strongly adhesively laminate.

The crosslinkers disclosed herein can be conveniently applied between selected films to be laminated using standard industry "glue" application processes, and then thermally activated to create a strong covalent bond.

Such covalently laminated films can be comprised of PE-to-PE (polyethylene-to-polyethylene), PP-to-PP (polypropylene-to-polypropylene) or PE-to-PP (polyethylene-to-polypropylene), where such covalent bonds are superior to prior art "glued" versions using specialized adhesives, as all glued together materials will ultimately fail, in time, if continually stress loaded. Also, moisture intrusion can act to de-laminate polymer film laminations, whereas covalently bonded interfaces are not subject to such delamination processes.

Application #3—Covalent Bonding of Polyolefin Film or Mesh to Polyimide Film by Topical Application Laminates comprised of mesh or webbing material fused or bonded to polymer films are used for sail materials to minimize weight and reduce tear propagation. One brand of such material is widely used and branded as "Dacron sailcloth". Material stretch and UV damage over time are key limitations of such woven fabrics used in an outdoor marine environment.

One of the few high tensile strength polymer films which is also highly UV resistant is BOPI (biaxially oriented polyimide). However, adhesively bonding such film to, for example, a high tensile strength mesh of webbing comprised of oriented UHMWPE fibres, is difficult. Such bonding can be effected using at least one of the crosslinkers disclosed herein.

Application #4—Pressure Infusion of Crosslinkers into Polyolefin Films

Polyolefin films are used globally for packaging, including for food packaging.

The tensile strength, low surface energy, tear strength, gas diffusion and UV degradation are some of the key parameters which limit the use of these films.

Such parameters can be modified by the incorporating at least one of the crosslinkers disclosed herein into the material itself.

Application #5—Direct Addition of Crosslinkers into the Polymer Melt or Extrudant Addition of one or more of the crosslinkers disclosed herein to a polymer melt or extrudant, followed by initiation of crosslinking by thermal, photochemical, or other means either during the extrusion process or following extrusion, can be used to control the material properties of the final polymer object.

Application #6—Pressure or Solvent Infusion of Crosslinkers into UHMWPE for Medical Implants Shaped UHMWPE constructs are currently used as protheses in medical implants. Such prior art implants have been modified using gamma-irradiation to increase material tensile strength. Such treatment using radiation is expensive, and thus limits widespread use.

Pressure or solvent infusion of at least one of the crosslinkers described herein, followed by low-temperature activation (70-110° C.), provides a convenient, cost-effective method to modify such UHMWPE prostheses.

Application #7—Pressure or Solvent Infusion of Crosslinkers into UHMWPE Woven or Non-Woven, Fabrics, etc Such UHMWPE constructs, comprised of fibres braided into lines or ropes, and woven, non-woven or knitted articles, have a number of potential commercial applications.

For example, 100 gsm (gram per square metre) plain woven UHMWPE fabric, which has utility for ballistic protective garments, can be modified by the pressure or solvent infusion of at least one f the crosslinkers described herein which, when activated, can increase the material tensile strength in both the MD (machine direction) and TD (transverse machine direction) by a factor of 2, preferably by a factor of 5 or more. This significant increase in material tensile strength acts to increase the material ballistic resistance properties without significantly increasing material weight.

Besides ballistic applications, such crosslinker-modified woven fabric can also be used for articles such as high strength sails, tents, tarps, kites, carry bags, backpacks, etc.

Application #8—Pressure or Solvent Infusion of Crosslinkers into Braided UHMWPE Lines and Ropes Lines and ropes made from braided fibres and strands of UHMWPE can be modified by the pressure infusion of at least one of the crosslinkers disclosed herein.

Similarly, pressure moulded films of UHMWPE can be stretched to create unidirectional films, which can be infused with one or more of the crosslinkers disclosed herein which, once activated, increases the tensile strength of such a film. Such film can be cut into narrow strips and woven into apparel, for example, for use as ballistic apparel, or other articles such as sails, tarps, etc.

Application #9—Topical and Pressure Infusion of Crosslinkers into PHC

In another application, the low energy requirement for the insertion of the crosslinkers described herein between the strong C—H bond enables the conversion of PHC (polyhydridocarbyne) to DLC (diamond-like carbon).

This conversion process currently requires the use of high temperature inert gas annealing, at temperatures of about 1,000° C. for several hours.

The infusion of at least one of the crosslinkers disclosed herein into the PHC (in powder form or in film form) provides for a new and elegant method to convert PHC to DLC, where such a DLC structure represents a completely new form of DLC.

Application #10—3D-Printing

The 3D-printing of a wide array of articles using various thermoplastic polymers has expanded rapidly, with diverse applications of this elegant technology. However, the physical properties of such printed polymer articles are limited by the inherent properties of the polymers used during printing.

The opportunity to modify the physical properties of a printed polymer article by thermal activation, UV activation, or activation through the use of an applied electric field, using at least one of the crosslinkers disclosed herein provides the user with heretofore new commercial possibilities.

Application #11—Crosslinkers as a Natural Foaming Agent

The crosslinkers disclosed herein can act as natural foaming aunts, due to the release of nitrogen gas during activation. When embedded into a polymer formulation of appropriate viscosity, activation of an appropriate amount of the crosslinker allows control of foaming parameters (expansion, density etc.).

EXAMPLES

General Considerations

All commercial materials were used as received. Reagents used in the synthesis of the compounds were purchased from Millpore Sigma except trimethyl(trifluoromethyl)silane (TMS-$CF_3$) which was purchased from ChemImpex.

All reactions were conducted in oven-dried glass ware. THF was freshly dried over Na/benzophenone. Dichloromethane (DCM) was freshly dried over $CaCl_2$ or by passage over alumina in a commercial solvent purification system. Anhydrous cyclohexane was used in crosslinking experiments. Spectranalyzed™ pentane/hexane was used for purification of bisdiazirines and crosslinked products.

$^{1}H$, $^{13}C$ NMR, and $^{19}F$ spectra were recorded at ambient temperature using either Bruker AVANCE 300 spectrometer or Bruker AVANCE Neo 500 spectrometer. Chemical shifts in $^{1}H$ and $^{13}C$ NMR spectra are reported in parts per million (ppm) and were referenced to residual protons of NMR solvents relative to tetramethylsilane. $^{1}H$ NMR data is presented in the format: chemical shift, (multiplicity (s=singlet, d=doublet, t=triplet, q=quartet pentet, qd=quartet of doublet, dt=doublet of triplet, ddd=doublet of doublet of doublet, ddt=doublet of doublet of triplet, m=multiplet, br s=broad singlet), coupling constant J in Hertz, integration). $^{13}C$ NMR data is presented in the same format as $^{1}H$ NMR data with the observed coupling pattern. Chemical shifts in $^{19}F$ spectra are reported in ppm and reported as obtained. Unless otherwise stated $^{19}F$ spectra are $^{1}H$ decoupled spectra.

IR spectra were recorded using a Perkin-Elmer ATR spectrometer. IR wave numbers (v) are reported in $cm^{-1}$. High resolution electrospray ionization mass spectrometry (HRMS) data were acquired using a Thermo Scientific Orbitrap Exactive Plus spectrometer.

Example 1: Synthesis of 1,1'-(1,3-phenylene)bis(2,2,2-trifluoroethan-1-ol)

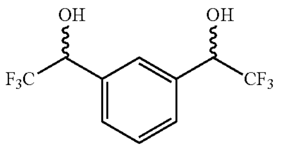

Chemical Formula: $C_{10}H_8F_6O_2$
Exact Mass: 274.0428
Molecular Weight: 274.1624

To a stirred solution of isophthalaldehyde (10.00 g, 74.55 mmol) in dry THF (150 mL) at 0° C. under argon, TMS-$CF_3$ (24.2 mL, 164.0 mmol) was added dropwise over 10 min. After stirring the reaction mixture for 5 minutes, 1.0 M tetrabutylammonium fluoride in THF (1.86 mL, 0.025 mmol) was added dropwise, and the reaction mixture gradually warmed to room temperature. Stirring was continued for 17 h. The reaction mixture was then poured into 3 M HCl (400 mL) and stirred vigorously for 24 h. The resultant solution was extracted with DCM (3×250 mL). The organic layers were combined, subsequently washed with water (1×30 mL) and brine (1×30 mL), dried over $Na_2SO_4$, filtered, and concentrated in vacuo to afford a light yellow solid. The product (20.2 g, 99%) was obtained as a diastereomeric mixture. $^{1}H$ NMR (500.27 MHz, chloroform-d) δ

7.61 (d, J=9.0 Hz, 1H), 7.57-7.51 (m, 2H), 7.47 (ddd, J=8.6, 6.8, 1.8 Hz, 1H), 5.07 (app. p, J=6.4 Hz, 2H), 2.67 (d, J=4.2 Hz, 2H). $^{13}C$ NMR (126 MHz, chloroform-d) δ 135.3, 128.4 and 128.4, 128.3 and 128.2, 126.7, 124.5 (q, J=282.3 Hz), 71.9 (q, J=31.4 Hz), 71.9 (q, J=31.7 Hz). $^{19}F$ NMR (282.54 MHz, chloroform-d) δ −78.44, −78.45. IR (diamond-ATR) v: 3355, 1437, 1258, 1164, 1118, 1060, 706. HRMS (ESI+) m/z [M+Na] calculated for $C_{10}H_8F_6O_2Na$: 297.03206. found: 297.03211.

Example 2: Synthesis of 1,1'-(1,3-phenylene)bis(2,2,2-trifluoroethan-1-one)

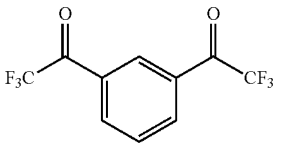

Chemical Formula: $C_{10}H_4F_6O_2$
Exact Mass: 270.0115
Molecular Weight: 270.1304

To a stirred solution of the product of Example 1 (20.14 g, 74.56 mmol) in 1,2-dichloroethane (200 mL), $MnO_2$ (32.40 g, 372.8 mmol) was added at room temperature under argon. The reaction mixture was then heated to reflux for 24 h. Upon completion of the reaction, the reaction mixture was filtered through a celite pad and the residue washed with DCM (2×50 mL). The filtrate was concentrated in vacuo to afford a light yellow oil which was directly loaded onto silica gel and eluted with diethyl ether. The product (18.01 g, 89%) was isolated as clear colourless oil. $^{1}H$ NMR (300.27 MHz, chloroform-d) δ 8.76 (s, 1H), 8.40 (d, J=7.6 Hz, 2H), 7.81 (t, J=7.9 Hz, 1H). 13C NMR (76 MHz, chloroform-d) δ 179.5 (q, J=36 Hz), 136.3-136.1 (m), 131.7-131.5 (m), 131.0, 130.4, 116.5 (q, J=291 Hz). $^{19}F$ NMR (282.54 MHz, chloroform-d) δ −71.76. IR (diamond-ATR) v: 1725, 1600, 1438, 1199, 1134, 730, 684.

Example 3: Synthesis of 1,1'-(1,3-phenylene)bis(2,2,2-trifluoroethan-1-one)dioxime

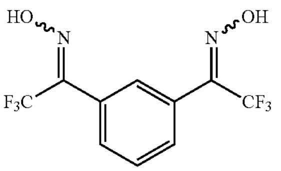

Chemical Formula: $C_{10}H_6F_6N_2O_2$
Exact Mass: 300.0333
Molecular Weight: 300.1604

To a stirred solution of the product of Example 2 (18.00 g, 66.63 mmol) in ethanol, hydroxylamine hydrochloride (27.80 g, 399.8 mmol) was added and the reaction mixture was heated to reflux for 2 h. Then mixture was then cooled to room temperature and adjusted to PH ~7 with aqueous 8 M NaOH solution, then heated to reflux for another 2 h. After cooling the reaction mixture to room temperature, it was concentrated in vacuo. The resultant residue was partitioned between water and diethyl ether. Layers were separated, and the aqueous layer further extracted with diethyl ether (4×200 mL). The organic layers were combined, dried over $Na_2SO_4$, filtered, and concentrated in vacuo to give the product (20 g, 100%) as a colourless solid which was predominately one of the syn- or anti-isomers. $^{1}H$ NMR (300.27 MHz, chloroform-d) δ 8.00 (br s, 2H), 7.67 (s, 1H), 7.65-7.54 (m, 3H). $^{13}C$ NMR (75.50 MHz, chloroform-d+methanol-$d_4$) δ 145.5 (p, J=32 Hz), 130.4, 129.2, 128.5, 127.2, 120.9 (q, J=274 Hz). $^{19}F$ NMR (282.54 MHz, chloroform-d) δ −66.53. IR (diamond-ATR) v: 3279, 1456, 1191, 1129, 960, 727. HRMS (ESI−) m/z [M−H] calculated for $C_{10}H_8F_6N_2O_2$: 299.02552. found: 299.02584.

Example 4: Synthesis of 1,1'-(1,3-phenylene)bis(2,2,2-trifluoroethan-1-one) O,O-ditosyl dioxime

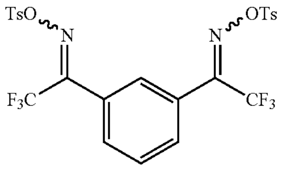

Chemical Formula: $C_{24}H_{18}F_6N_2O_6S_2$
Exact Mass: 608.0510
Molecular Weight: 608.5264

To a stirred solution of the product of Example 3 (20.00 g, 66.63 mmol) in dry DCM (200 mL) at 0° C. under argon, triethylamine (27.9 mL, 200 mmol), p-toluenesulfonyl chloride (26.04 g, 136.59 mmol) and DMAP (0.16 g, 1.33 mmol) were added sequentially. The reaction was gradually warmed to room temperature and stirred for 1 h. The reaction mixture was then diluted with DCM (200 mL) and washed sequentially with 1 M HCl (2×20 mL), water (1×20 mL), and brine (1×20 mL). The organic layer was dried over $Na_2SO_4$, filtered, and concentrated in vacuo to give the product (37.33 g, 92% yield) as a colourless solid which was predominately one of the syn- or anti-isomers. 1H NMR (300.27 MHz, chloroform-d) δ 7.89 (d, J=8.4 Hz, 4H), 7.68-7.53 (m, 3H), 7.40 (d, J=8.1 Hz, 4H), 7.36 (s, 1H), 2.49 (s, 6H). $^{13}C$ NMR (126 MHz, chloroform-d) δ 152.4 (p, J=34 Hz), 146.6, 131.8, 131.0, 130.2, 129.8, 129.5, 128.2, 125.6, 119.5 (q, J=278 Hz), 22.0. $^{19}F$ NMR (282.54 MHz, chloroform-d) δ −66.69. IR (diamond-ATR) v: 1596, 1456, 1394, 1193, 1179, 1145, 1090, 1034, 904, 814, 756, 674, 544. HRMS (ESI+) m/z [M+Na] calculated for $C_{24}H_{18}F_6N_2O_6S_2Na$: 631.04027. found: 631.03997.

Example 5: Synthesis of 1,3-bis(3-(trifluoromethyl)diaziridin-3-yl)benzene

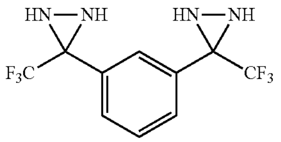

Chemical Formula: $C_{10}H_8F_6N_4$
Exact Mass: 298.0653
Molecular Weight: 298.1924

$NH_3$ gas was condensed (~80 mL) at −78° C. into a 500 mL three neck round bottom flask equipped with dewar, inlet and outlet for gas flow. In order to get dry $NH_3$ the gas was passed through tubing that contained layers of KOH pellets. To this liquid $NH_3$, a solution of the compound of Example 4 (2.00 g, 3.29 mmol) in dry DCM (6 mL) was added dropwise over 10 min, using a cannula. The reaction was maintained at −78° C. for 6 h and then gradually allowed to warm to room temperature. After complete evaporation of excess $NH_3$, a white suspension was formed. To this, water (30 mL) and DCM (120 mL) were added. The organic layer was separated and washed subsequently with water (2×20 mL) and brine (1×20 mL), dried over $Na_2SO_4$, filtered, and concentrated in vacuo to give a crude product which was purified by silica gel chromatography. The product (0.85 g, 87%) was isolated as white solid. 1H NMR (500.27 MHz, chloroform-d) δ 7.89 (s, 1H), 7.73 (d, J=7.8 Hz, 2H), 7.51 (t, J=7.8 Hz, 1H), 2.85 (d, J=8.9 Hz, 2H), 2.26 (d, J=8.9 Hz, 2H). $^{13}$C NMR (126 MHz, chloroform-d) δ 132.7 and 132.7, 130.2 and 130.1, 129.5, 128.1 and 128.0, 123.4 (q, J=274 Hz), 123.5 (q, J=274 Hz), 58.0 (q, J=36 Hz) 57.9 (q, J=36 Hz). 19F NMR (470.72 MHz, chloroform-d) δ −75.30, −75.37. IR (diamond-ATR) ν: 3253, 3206, 3182, 1395, 1225, 1136, 953, 724, 654. HRMS (ESI−) m/z [M−H] calculated for $C_{10}H_7F_6N_4$: 297.05802. found: 297.05795.

Example 6: Synthesis of 1,3-bis(3-(trifluoromethyl)-3H-diazirin-3-yl)benzene (or "CL-PH")

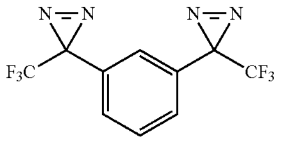

Chemical Formula: $C_{10}H_4F_6N_4$
Exact Mass: 294.0340
Molecular Weight: 294.1604

To a stirring solution of the compound of Example 5 (1.00 g, 3.35 mmol) in DCM (20 mL) at 0° C. under argon, triethylamine (2.80 mL, 20.1 mmol) was added. To this, iodine (1.87 g, 7.37 mmol) was added in three portions and the reaction stirred at 0° C. for 1 h. The reaction mixture was diluted with 20 mL DCM and washed with 1 M NaOH (1×20 mL), and water (2×20 mL). The organic layer was dried over $Na_2SO_4$, filtered, and concentrated carefully under low vacuum at <10° C. (rotary evaporator water bath was filled with ice+water) to give a crude product which was purified through silica gel chromatography. The desired product was eluted with pentane and the compound-containing pentane fractions were concentrated under low vacuum at <10° C. (0.80 g, 82% yield). $^1$H NMR (500.27 MHz, chloroform-d) δ 7.47 (t, J=7.9 Hz, 1H), 7.31 (d, J=8.7 Hz, 2H), 6.92 (s, 1H). $^{13}$C NMR (126 MHz, chloroform-d) δ 130.4, 129.7, 128.0, 125.3, 122.0 (q, J=274 Hz), 28.4 (q, J=41 Hz). $^{19}$F NMR (470.72 MHz, chloroform-d) δ −65.23. IR (diamond-ATR) ν: 1610, 1588, 1495, 1330, 1179, 1147, 792, 694. HRMS (ESI−) m/z [M−H] calculated for $C_{10}H_3F_6N_4$: 293.02672. found: 293.02684.

Example 7: Synthesis of Dimethyl Pyridine-3,5-Dicarboxylate

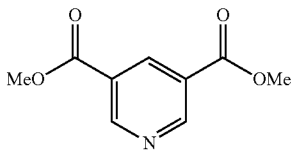

Chemical Formula: $C_9H_9NO_4$
Exact Mass: 195.0532
Molecular Weight: 195.1740

To a stirred suspension of 3,5-pyridinedicarboxylic acid (8.00 g, 47.90 mmol) in methanol (160 mL) at room temperature, $SOCl_2$ (10.42 mL, 143.7 mmol) was added dropwise. The mixture was heated to reflux. Within 30 minutes the suspension became a solution which was stirred under reflux for another 3 h. After cooling the reaction mixture to room temperature, the contents were concentrated in vacuo. To the resulting residue, water was added and adjusted pH~7 with aqueous 8 M NaOH solution. The resulted suspension was extracted with EtOAc (3×100 mL). The organic layers were combined, washed subsequently with saturated $NaHCO_3$ (2×30 mL), water (1×30 mL) and brine (1×30 mL), dried over $Na_2SO_4$, filtered, and concentrated in vacuo to give a white solid (9.2 g, 98%). $^1$H NMR (300.27 MHz, chloroform-d) δ 9.36 (d, J=2.1 Hz, 2H), 8.87 (t, J=2.1 Hz, 1H), 3.99 (s, 6H). $^{13}$C NMR (75.50 MHz, chloroform-d) δ 165.0, 154.4, 138.2, 126.1, 52.9. IR (diamond-ATR) ν: 3087, 3012, 2962, 1716, 1602, 1264, 743, 691.

Example 8: Synthesis of 1,1'-(pyridine-3,5-diyl)bis(2,2,2-trifluoroethan-1-one)dioxime

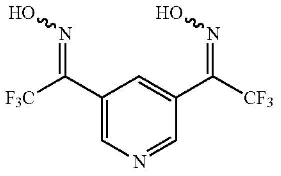

Chemical Formula: $C_9H_5F_6N_3O_2$
Exact Mass: 301.0286
Molecular Weight: 301.1484

In a flame-dried flask under argon, to a solution of dimethyl pyridine-3,5-dicarboxylate (1 eq., 1.00 g, 5.12 mmol) and $TMSCF_3$ (5.0 eq., 3.79 mL, 25.6 mmol) in dry DCM (4 mL, distilled) at −15° C. (ice/ethanol bath) was added dropwise a 1M solution of TBAF in THF (5 mol %, 256 μL, 256 μmol). The mixture was stirred for 1 h, giving a clear, dark reaction mixture. At 30 min, TLC and NMR showed that reaction was complete.

The reaction was quenched at −15° C. by the addition of ethanol (25 mL), followed by hydroxylamine hydrochloride (6.15 eq., 2.19 g, 31.5 mmol). The mixture was brought to pH 11 with 2 M aq. NaOH (12 eq., 30 mL, 61.5 mmol), heated to reflux for 2 h and then left at room temperature overnight (12 h). The mixture was then neutralized (pH=7-8) by the addition of small portions of 4 M HCl, and concentrated to remove most of the ethanol. The aqueous mixture was then treated with sat. aq. ammonium chloride (50 mL) and extracted with diethyl ether (3×50 mL). The combined organic extracts were washed with brine (50 mL), dried with sodium sulfate, filtered and concentrated. The residue was purified by silica gel column chromatography (gradient of AcOEt/hexanes from 5% to 50%) to afford the desired bis-oxime (1.22 g, 4.03 mmol) in 79% yield over 2 steps. 1H NMR (300.27 MHz, acetone-$d_6$) δ 12.26 (s, 1H), 8.87 (d, J=2.0 Hz, 2H), 8.13 (t, J=2.0 Hz, 1H), 2.85 (s, 1H). $^{13}C$ NMR (126 MHz, acetone-$d_6$) δ 151.4, 143.8 (q, J=32.9 Hz), 137.5, 124.2, 121.8 (q, J=273.0 Hz). $^{19}F$ NMR (282.54 MHz, acetone-$d_6$) δ −67.00. IR (diamond-ATR) ν: 3184, 3054, 2853, 1693, 1584, 1343, 1249, 1195, 1121, 969, 732. HRMS (ESI+) m/z [M+H] calculated for $C_9H_6F_6N_3O_2$: 302.03587. found: 302.0359.

Example 9: Synthesis of 1,1'-(pyridine-3,5-diyl)bis(2,2,2-trifluoroethan-1-one) O,O-ditosyl dioxime

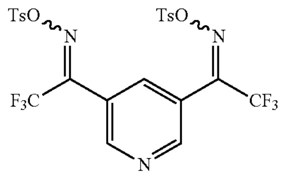

Chemical Formula: $C_{23}H_{17}F_6N_3O_6S_2$
Exact Mass: 609.0463
Molecular Weight: 609.5144

To a suspension of the product of Example 8 (1 eq., 1.181 g, 3.92 mmol) in DCM (10 mL) at room temperature was added tosyl chloride (2.1 eq., 1.57 g, 8.23 mmol), triethylamine (3.0 eq., 1.64 mL, 11.8 mmol), and DMAP (5 mol %, 24 mg, 196 μmol). The mixture was stirred at room temperature for 1.5 h. The mixture was treated with sat. aq. $NH_4Cl$ (50 mL) and extracted with DCM (3×50 mL). The combined organic extracts were washed with water (50 mL), dried with sodium sulfate, filtered, and concentrated. The residue was purified by silica gel column chromatography (gradient of AcOEt/hexanes from 0% to 20%) to afford the desired bis-tosyloxime (2.23 g, 3.65 mmol) in 93% yield. 1H NMR (500.27 MHz, chloroform-d) δ 8.79 (d, J=2.1 Hz, 2H), 7.90 (d, J=8.4 Hz, 4H), 7.77 (s, 1H), 7.41 (d, J=8.1 Hz, 4H), 2.49 (s, 6H). $^{13}C$ NMR (126 MHz, chloroform-d) δ 151.41, 149.8 (q, J=34.9 Hz), 146.9, 136.1, 130.7, 130.3, 129.5, 121.6, 119.3 (q, J=278 Hz), 22.0. $^{19}F$ NMR (282.54 MHz, chloroform-d) δ −66.58. IR (diamond-ATR) ν: 1597, 1394, 1197, 1181, 1151, 902, 815, 763, 685, 548. HRMS (ESI+) m/z [M+H] calculated for $C_{23}H_{18}F_6N_3O_6S_2$: 610.0536. found: 610.0535; [M+Na] calculated for $C_{23}H_{17}F_6N_3O_6S_2Na$: 632.0355. found: 632.0352.

Example 10: Synthesis of 3,5-bis(3-(trifluoromethyl)diaziridin-3-yl)pyridine

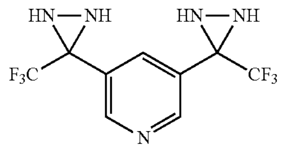

Chemical Formula: $C_9H_7F_6N_5$
Exact Mass: 299.0606
Molecular Weight: 299.1804

A flame-dried 3-neck flask under argon was equipped with a gas condenser and a circulation of anhydrous gaseous ammonia was set up. Upon cooling the system to −78° C., ca. 125 mL of ammonia (ca. 1500 eq.) was condensed in the flask. A solution of the compound of Example 9 (1 eq., 2.19 g, 3.59 mmol) in anhydrous $CH_2Cl_2$ (10 mL) at room temperature was added dropwise over 10 min, maintaining the gaseous ammonia flow. The reaction mixture was stirred at −78° C. for 1 h. The mixture was allowed to warm up to room temperature over 1.5 h (a room temp water bath was used in the last hour). When the ammonia had all evaporated, water (50 mL) and $CH_2Cl_2$ (50 mL) were added to the flask and the layers separated. The aqueous layer was further extracted with $CH_2Cl_2$ (5×50 mL). The combined organic extracts were dried with sodium sulfate, filtered, and concentrated. The crude residue was purified by silica gel column chromatography (gradient of AcOEt/hexanes from 20% to 45%) to afford the desired bis-diaziridine (806 mg, 2.69 mmol) with 75% yield. $^1H$ NMR (300.27 MHz, methylene chloride-$d_2$) δ 8.96 (d, J=2.1 Hz, 2H), 8.20 (s, 1H), 2.98 (d, J=8.9 Hz, 2H), 2.39 (d, J=8.9 Hz, 2H). 13C NMR (126 MHz, acetone-$d_6$) δ 151.6 and 151.6, 137.4, 137.2, 129.3 and 129.2, 124.8 (q, J=278 Hz), 57.0 (q, J=36.4 Hz), 56.9 (q, J=36.4 Hz). $^{19}F$ NMR (282.54 MHz, methylene chloride-$d_2$) δ −75.66. IR (diamond-ATR) ν: 3210, 1586 1440, 1394, 1145, 718, 671. HRMS (ESI+) m/z [M+H] calculated for $C_9H_8F_6N_5$: 300.06784. found: 300.0678.

Example 11: Synthesis of 3,5-bis(3-(trifluoromethyl)-3H-diazirin-3-yl)pyridine (or "CL-PY")

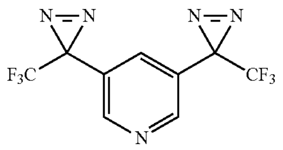

Chemical Formula: $C_9H_3F_6N_5$
Exact Mass: 295.0293
Molecular Weight: 295.1484

Reaction and workup were performed as in synthesis of Example 6. Materials used in the reaction: the compound of Example 10 (0.40 g, 1.34 mmol) in DCM (10 mL), triethylamine (1.12 mL, 8.04 mmol), and iodine (0.75 g, 2.95 mmol). The product (0.30 g, 75% yield) was obtained as clear colourless liquid which solidified upon cooling. $^1H$ NMR (300.27 MHz, methylene chloride-$d_2$) δ 8.61 (s, 2H), 7.29 (s, 1H). $^{13}C$ NMR (126 MHz, methylene chloride-$d_2$) δ 149.5 (q, J=2.0 Hz), 132.9, 125.9, 122.0 (q, J=275 Hz), 27.4 (q, J=42.0 Hz). $^{19}F$ NMR (282.54 MHz, methylene chloride-$d_2$) δ −65.89. IR (diamond-ATR) ν: 3058, 3025, 2949, 1622, 1452, 1332, 1260, 1181, 1144, 707, 681. HRMS (ESI+) m/z [M+H] calculated for $C_9H_4F_6N_5$: 296.03654. found: 296.03655.

Example 12: Synthesis of dimethyl 4,4'-(perfluoropropane-2,2-diyl)dibenzoate

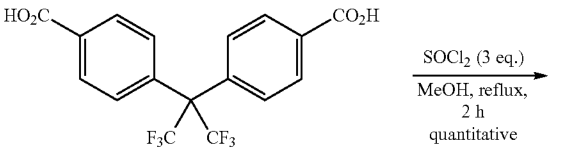

Chemical Formula: $C_{17}H_{10}F_6O_4$
Exact Mass: 392,05
Molecular Weight: 392,25

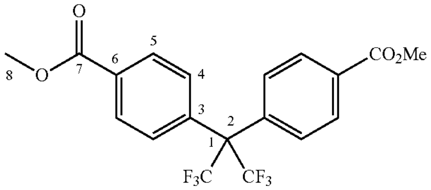

Chemical Formula: $C_{19}H_{14}F_6O_4$
Exact Mass: 420,08
Molecular Weight: 420,31

To a solution of 4,4'-(perfluoropropan-2,2-diyl)dibenzoic acid (10.00 g, 25.49 mmol) in MeOH (100 mL) was added dropwise thionyl chloride (3 eq., 5.55 mL, 76.48 mmol) at room temperature. The clear, colorless reaction mixture was stirred under reflux for 2 h. The mixture was cooled down to room temperature and then concentrated in vacuo. The residue was treated with sat. aq. sodium bicarbonate (50 mL) and extracted with $Et_2O$ (3×50 mL). The combined organic layers were washed with brine (50 mL), dried over sodium sulfate and concentrated to afford a colorless resin (10.72 g, 25.49 mmol, quantitative). $^{1}$H NMR (300 MHz, chloroform-d) δ 8.05 (d, J=8.4 Hz, 4H, H-5), 7.46 (d, J=8.4 Hz, 4H, H-4), 3.94 (s, 6H, H-8). $^{13}$C NMR (75 MHz, chloroform-d) δ 166.25 (C-7), 137.70 (C-3), 131.15 (C-6) 130.37 (C-4), 129.58 (C-5), 123.96 (q, J=296 Hz, C-1), 64.68 (m, J=26 Hz, C-2), 52.53 (C-8). $^{19}$F NMR (282 MHz, chloroform-d) δ −63.51. IR (diamond-ATR) v: 2956, 1726, 1612, 1577, 1513, 1438, 1417, 1326, 1279, 1252, 1239, 1208, 1171, 1111, 1022, 972, 959, 945, 929, 853, 825, 768, 748, 721, 709, 688. HRMS (ESI+) m/z [M+H] calculated for $C_{19}H_{15}F_6O^4$: 421.08690. found: 421.08689.

Example 13: Synthesis of 3,3'-((perfluoropropane-2,2-diyl)bis(4,1-phenylene))bis(3-(trifluoromethyl) diaziridine)

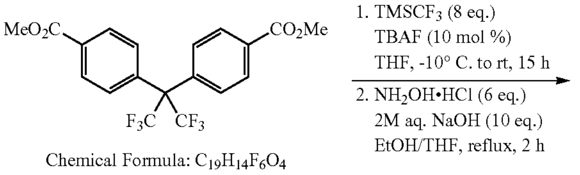

Chemical Formula: $C_{19}H_{14}F_6O_4$
Exact Mass: 420,08
Molecular Weight: 420,31

-continued

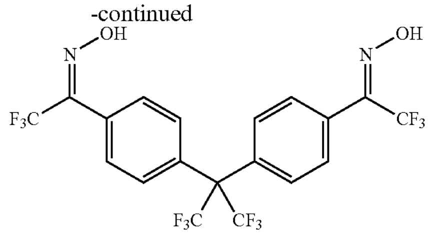

Chemical Formula: $C_{19}H_{10}F_{12}N_2O_2$
Exact Mass: 526,06
Molecular Weight: 526,28

In a flame-dried flask under argon, to a stirred solution of the product of Example 12 (1 eq., 10.12 g, 24.08 mmol) and $TMSCF_3$ (8.0 eq., 28.47 mL, 192.6 mmol) in anhydrous THF (60 mL) at −10° C. (ice/ethanol bath) was added dropwise a 1 M solution of TBAF in THF (10 mol %, 2.41 mL, 2.41 mmol). The mixture was then stirred, allowing the temperature to slowly raise to room temperature. As the temperature rose, the solution turned darker and darker orange.

The mixture was quenched by the slow, careful addition of ethanol (80 mL). Hydroxylamine hydrochloride (6 eq., 10.04 g, 144.5 mmol) was added to the mixture, followed by the subsequent addition of 2 M aq. NaOH (16.6 eq., 200 mL, 400 mmol). The mixture was heated to reflux for 1 h. The pH was neutralized by the addition of small portions of 4 M aq. HCl, then the mixture was concentrated to remove most of THF and EtOH. The resulting aqueous mixture was treated with sat. aq. $NH_4Cl$ (100 mL) diluted with a bit of water to prevent precipitation, and extracted with $Et_2O$ (3×150 mL). TLC confirmed efficient extraction. The combined organic extracts were then dried with sodium sulfate, filtered and concentrated. Then the residue was dried under high vacuum for prolonged time with some gentle heating to afford a foam.

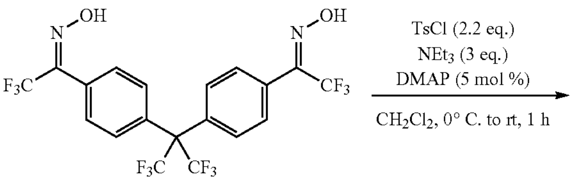

Chemical Formula: $C_{19}H_{10}F_{12}N_2O_2$
Exact Mass: 526,05507
Molecular Weight: 526,28184

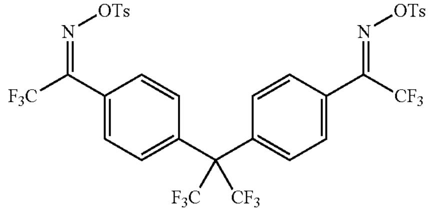

Chemical Formula: $C_{33}H_{22}F_{12}N_2O_6S_2$
Exact Mass: 834,07277
Molecular Weight: 834,64784

The impure foamy residue from above (1 eq., 16.37 g) was dissolved in DCM (50 mL), and triethylamine (3.0 eq., 13.01 mL, 93.32 mmol), DMAP (5 mol %, 190 mg, 1.55 mmol) and tosyl chloride (2.2 eq., 13.05 g, 68.43 mmol) were successively added at 0° C. The ice bath was removed after 5 min and the reaction mixture was stirred at room temperature for 1 h. The mixture was then treated with sat. aq. $NH_4Cl$ (100 mL) and extracted with DCM (3×100 mL). The combined organic extracts were dried with sodium sulfate, filtered, and concentrated. The residue was quickly purified by silica gel column chromatography (gradient of AcOEt/hexanes from 5% to 40%) to remove the excess tosyl chloride and afford a crude product.

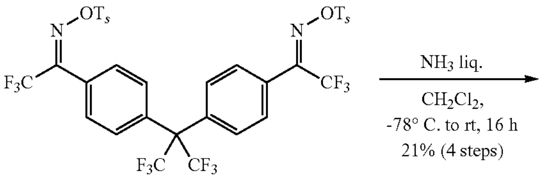

Chemical Formula: $C_{33}H_{22}F_{12}N_2O_6S_2$
Exact Mass: 834,07
Molecular Weight: 834,65

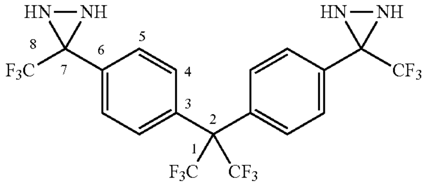

Chemical Formula: $C_{19}H_{12}F_{12}N_4$
Exact Mass: 524,09
Molecular Weight: 524,31

A flame-dried 3-neck flask under argon was equipped with a gas condenser and a circulation of anhydrous gaseous ammonia was set up. Upon cooling the system to −78° C., ca. 250 mL of ammonia (ca. 350 eq.) was condensed in the flask. A solution of the crude product obtained above in DCM (100 mL) at room temperature was added dropwise over 20 min to the liquid ammonia at −78° C. The dry ice bath was removed so the reaction mixture could warm up to room temperature overnight (ca. 16 h), while ammonia was evaporating. When all the ammonia had evaporated, the resulting suspension in DCM was treated with sat. aq. $NH_4Cl$ (100 mL) and extracted with DCM (3×100 mL). The combined organic extracts were dried with sodium sulfate, filtered and concentrated. The residue was purified by silica gel column chromatography (gradient of AcOEt/hexanes from 5% to 25%) to afford the desired bis-diaziridine (2.70 g, 5.15 mmol) in 21% yield over 4 steps. 1H NMR (500 MHz, acetone-$d_6$) δ 7.78 (d, J=8.5 Hz, 4H, H-5), 7.50 (d, J=8.5 Hz, 4H, H-4), 3.77 (d, J=8.7 Hz, 2H, N—H), 3.52 (d, J=8.7 Hz, N—H). $^{13}C$ NMR (125 MHz, acetone-$d_6$) δ 135.11 (C-3 or C-6), 134.83 (C-3 or C-6), 131.03 (C-4), 129.68 (C-5), 125.04 (q, J=287 Hz, C-1), 125.03 (q, J=278 Hz, C-8), 65.34 (m, J=25 Hz, C-2), 58.13 (q, J=36 Hz, C-7). $^{19}F$ NMR (470 MHz, acetone-$d_6$) δ −64.16 (CF3-1), −75.55 (two s, CF3-8). IR (diamond-ATR) ν: 3231, 1701, 1519, 1398, 1255, 1248, 1206, 1172, 1097, 1025, 972, 943, 930, 882, 831, 742, 719, 708, 669, 576, 549, 477.

Example 14: Synthesis of 3,3'-((perfluoropropane-2,2-diyl)bis(4,1-phenylene))bis(3-(trifluoromethyl)-3H-diazirine) (or "CL-HF2PH")

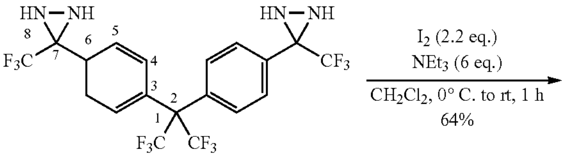

Chemical Formula: $C_{19}H_{12}F_{12}N_4$
Exact Mass: 524,09
Molecular Weight: 524,31

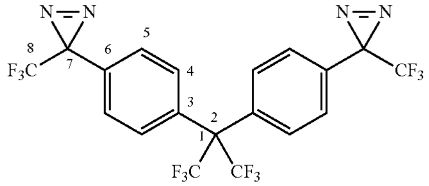

Chemical Formula: $C_{19}H_8F_{12}N_4$
Exact Mass: 520,06
Molecular Weight: 520,28

To a solution of the compound of Example 13 (1 eq., 1.10 g, 2.10 mmol) in DCM (50 mL) at 0° C. were added successively triethylamine (6 eq., 1.76 mL, 12.6 mmol) and iodine (2.2 eq., 1.17 g, 4.62 mmol). The colored mixture was stirred at 0° C. for 30 min, then at room temperature for another 30 min. The mixture was diluted with DCM (50 mL) and washed with a 1:1 mixture of sat. aq. sodium thiosulfate (25 mL) and water (25 mL). The phases were separated and the aqueous layer was re-extracted with DCM (50 mL). The organic extracts were combined and dried with sodium sulfate, filtered and concentrated. The residue was purified by silica gel column chromatography (solid deposit, elution with pentane) to afford the desired bis-diazirine (701.2 mg, 1.35 mmol) as a colorless oil in 64% yield. 1H NMR (300 MHz, dichloromethane-$d_2$) δ 7.41 (d, J=8.5 Hz, 4H, H-5), 7.23 (d, J=8.5 Hz, 4H, H-4). 13C NMR (125 MHz, dichloromethane-$d_2$) δ 134.75 (C-3), 130.98 (C-5), 130.87 (C-6), 126.86 (C-4), 124.23 (q, J=287 Hz, C-1), 122.39 (q, J=275 Hz, C-8), 64.68 (m, J=26 Hz, C-2), 28.56 (q, J=41 Hz, C-7). 19F NMR (282 MHz, dichloromethane-$d_2$) δ −64.07 (CF3-1), −65.52 (CF3-8). IR (diamond-ATR) ν: 2362, 2093, 1729, 1616, 1522, 1351, 1338, 1289, 1207, 1177, 1153, 1055, 1025, 971, 942, 931, 875, 818, 746, 732, 709, 675, 553.

General Procedure for the Crosslinking of Cyclohexane $(CH_2)_6$, as a Small-Molecule Model for Linear Polyethylene $(CH_2)_n$ a) UV activation: a 1 mM solution of bisdiazirine in cyclohexane was prepared in a 500 mL round-bottom flask and the contents were flushed gently with argon. The flask was sealed with a septum and placed under a balloon of argon to maintain an inert atmosphere. The reaction was carried out at room temperature. The round bottom flask was suspended into a Rayonet UV chamber that was equipped with eight 350 nm UV lamps and an operating fan.

The reaction contents were irradiated for 4 h. Upon confirming the absence of peaks at ~−65 ppm (bisdiazirine) and ~−54 ppm (diazo species) in the $^{19}F$ NMR spectra (benzene-$d_6$), the reaction was concentrated in vacuo to provide crude product.

b) Thermal activation: a 10 mM solution of bisdiazirine in cyclohexane was placed in a 100 mL sealed tube, flushed gently with argon and capped. The mixture was heated with stirring at 140° C. for 2 h. After cooling the mixture to room temperature, the contents were transferred into a round bottom flask and concentrated in vacuo to provide crude product.

Example 15: Crosslinking of cyclohexane (1)—preparation of 1,3-bis(1-cyclohexyl-2,2,2-trifluoroethyl)benzene

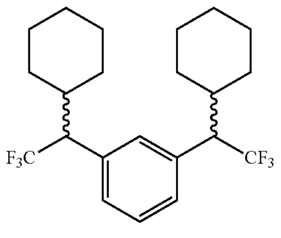

Chemical Formula: $C_{22}H_{28}F_6$
Exact Mass: 406.2095
Molecular Weight: 406.4564

Reactions were performed as described in the above general procedure for crosslinking experiments. UV activation reaction: the compound of Example 6 (102 mg in 347 mL cyclohexane) was used, and product (11.5 mg, 8.2%) was isolated following chromatography. Thermal activation reaction: the compound of Example 6 (121 mg in 40.8 mL cyclohexane) was used and product (14.3 mg, 8.6%) was isolated following chromatography. In both cases, crude material was purified in a similar manner as described herein and the product was isolated as mixture of diastereomers, as a light yellow oil. The crude product was dissolved in 10% diethyl ether in pentane (~2 mL), loaded onto a column packed with silica gel and eluted with pentane. Several 2-4 mL fractions were collected in 12×75 mm test tubes. Fractions that contain the product (as determined by $^1H/^{19}F$ spectra), were combined and concentrated together to give the product. 1H NMR (500.27 MHz, chloroform-d) δ 7.31 (t, J=7.7 Hz, 1H), 7.18 (d, J=7.7 Hz, 2H), 7.07 (s, 1H), 3.04 (qd, J=10.1, 8.1 Hz, 2H), 2.04-1.88 (m, 4H), 1.82-1.71 (m, 2H), 1.68-1.58 (m, 4H) 1.44 (d, J=12.4 Hz, 2H), 1.30 (qt, J=13.1, 3.5 Hz, 2H), 1.21-1.02 (m, 6H), 0.79 (qd, J=12.0, 3.3 Hz, 2H). $^{13}C$ NMR (126 MHz, chloroform-d) δ 135.5 (m), 130.5 and 130.4, 128.7, 128.6 and 128.5, 127.3 (q, J=281 Hz), 56.2 (q, J=25.1 Hz), 56.1 (q, J=25.1 Hz), 38.7, 31.7 (d, J=2.2 Hz), 30.8 (d, J=3.2 Hz), 26.3, 26.2, 26.2. $^{19}F$ NMR (470.72 MHz, chloroform-d) δ −63.39, −63.38. IR: 2926, 2855, 1451, 1252, 1151, 1102, 714. HRMS (ESI+) m/z [M+Na] calculated for $C_{22}H_{28}F_6Na$: 429.19929. found: 429.19918.

Example 16: Crosslinking of cyclohexane (2)—preparation of 3,5-bis(1-cyclohexyl-2,2,2-trifluoroethyl)pyridine

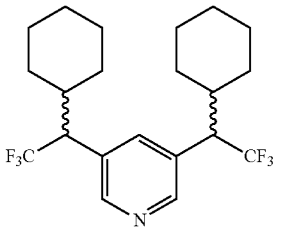

Chemical Formula: $C_{21}H_{27}F_6N$
Exact Mass: 407.2048
Molecular Weight: 407.4444

Reactions were performed as described in the above general procedure for crosslinking experiments. For UV activation reaction: the compound of Example 11 (97 mg in 328 mL solvent) was used, and product (10 mg, 7.4%) was isolated following chromatography. For thermal activation reaction: the compound of Example 11 (118 mg in 40 mL solvent) was used and product (12.3 mg, 7.5%) was isolated following chromatography. In both cases, crude material was purified in a similar manner as described herein and the product was isolated as mixture of diastereomers, as a light yellow solid. The crude product was dissolved in DCM (~1 mL) and loaded onto a column that was packed with silica gel and eluted with 12-15% EtOAc in hexane. $^1H$ NMR (500.27 MHz, chloroform-d) δ 8.44 (br s, 2H), 7.50 (d, J=10.2 Hz, 1H), 3.12 (ddt, J=14.4, 10.0, 5.0 Hz, 2H), 1.99 (m, 4H), 1.82-1.76 (m, 2H), 1.68-1.60 (m, 4H), 1.47 (d, J=12.7 Hz, 2H), 1.31 (qt, J=12.8, 3.5 Hz, 2H), 1.22-0.99 (m, 6H), 0.85-0.70 (m, 2H). $^{13}C$ NMR (126 MHz, chloroform-d) δ 150.2, 150.1, 136.9, 136.6, 130.8, 126.9 (q, J=281 Hz), 126.8 (q, J=281 Hz), 53.8 (q, J=25.8 Hz), 53.7 (q, J=25.8 Hz), 38.4, 31.6 (d, J=4.7 Hz), 30.7, 30.5, 26.2, 26.1, 26.0. $^{19}F$ NMR (470.72 MHz, chloroform-d) δ −63.55, −63.56. IR (diamond-ATR) v: 2928, 2856, 1452, 1252, 1154, 1101, 729. HRMS (ESI+) m/z [M+H] calculated for $C_{21}H_{28}F_6N$: 408.21205. found: 408.21202.

Example 17: Crosslinking of cyclohexane (3)—preparation of 4,4'-(perfluoropropane-2,2-diyl)bis((1-cyclohexyl-2,2,2-trifluoroethyl)benzene)

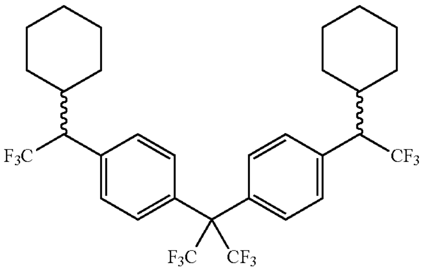

Chemical Formula: $C_{31}H_{32}F_{12}$
Exact Mass: 632.2312
Molecular Weight: 632.5778

Reactions were performed as described in the above general procedure for crosslinking experiments. Thermal activation under the standard conditions described above (with 115 mg CL-HF2PH in 22 mL cyclohexane at 140° C.) afforded 9.7 mg product (7% yield) following chromatography. Thermal activation was repeated under slightly modified conditions (81.1 mg in 15.6 mL solvent) at 110° C. for 7 h to produce the identical product (9.4 mg, 9.5%). In both cases, crude material was purified in a similar manner as previously described and the desired product was isolated as mixture of diastereomers, as a white solid. $^{1}H$ NMR (500.27 MHz, chloroform-d) δ 7.35 (d, J=8.4 Hz, 4H), 7.24 (d, J=8.4 Hz, 4H), 3.07 (p, J=9.7 Hz, 2H), 2.04-1.88 (m, 4H), 1.78 (m, 2H), 1.70-1.59 (m, 4H), 1.46 (d, J=13.1 Hz, 2H), 1.37-1.06 (m, 9H), 0.91-0.78 (m, 2H). $^{13}C$ NMR (126 MHz, chloroform-d) δ 136.4 (d, J=2.5 Hz), 132.8, 130.4, 129.2, 127.1 (q, J=280 Hz), 124.3 (q, J=282.54 Hz), 64.4 (q, J=25.1 Hz), 56.0 (q, J=25.3 Hz), 38.6, 31.6, 30.9, 26.3, 26.2, 26.1. $^{19}F$ NMR (470.72 MHz, chloroform-d) δ −63.21, −63.68 IR (diamond-ATR) v: 2926, 2855, 1519, 1453, 1250, 1176, 1155, 1100, 713. HRMS (ESI+) m/z [$M+CH_3CN+H$] calculated for $C_{33}H_{36}F_{12}N$: 674.26561. found: 674.26475.

Examples 15-17 serve as a clear demonstration that compounds of Formula I can be used to crosslink non-functionalized polymers.

Example 18: Crosslinking of Paraffin Wax (A Low Molecular Weight Polyethylene)

Material used: paraffin wax from Sigma-Aldrich (ref 327212, m.p.=58-62° C., CAS 8002-74-2)

Procedure: 8 samples were prepared by mixing molten wax (above 60° C.) with CL-HF2PH in various ratios (see table below). For each sample, the two products were added to the same vial and then melted together by using a mild heating from a heat gun, or a water bath set up slightly above 60° C. The following mixtures were prepared:

Composition of crosslinked paraffin wax samples with CL-HF2PH.

| Sample | Loading (w %) | Mass wax (mg) | Mass CL (mg) | Total mass (mg) |
|---|---|---|---|---|
| A | 0 | 200 | 0 | 200 |
| B | 0 | 200 | 0 | 200 |
| C | 1 | 200 | 2 | 202 |
| D | 5 | 200 | 10 | 210 |
| E | 20 | 100 | 20 | 120 |
| F | 50 | 50 | 25 | 75 |
| G | 100 | 50 | 50 | 100 |
| H | 200 | 25 | 50 | 75 |

All samples were opaque, white and solid at room temperature. Samples B-H were placed in an oven at 110° C. for 16 h. Sample A was kept at room temperature. A portion of each of the samples (10 mg) was covered with THF (1.0 mL). After shaking for ca. 1 h, all samples but sample H dissolved completely. The latter (highest crosslinker loading) did not fully dissolve, leaving a swollen material (see FIG. 7). The dissolved samples were analyzed by gel permeation chromatography (CPC) using THF as mobile phase.

Figure 7:
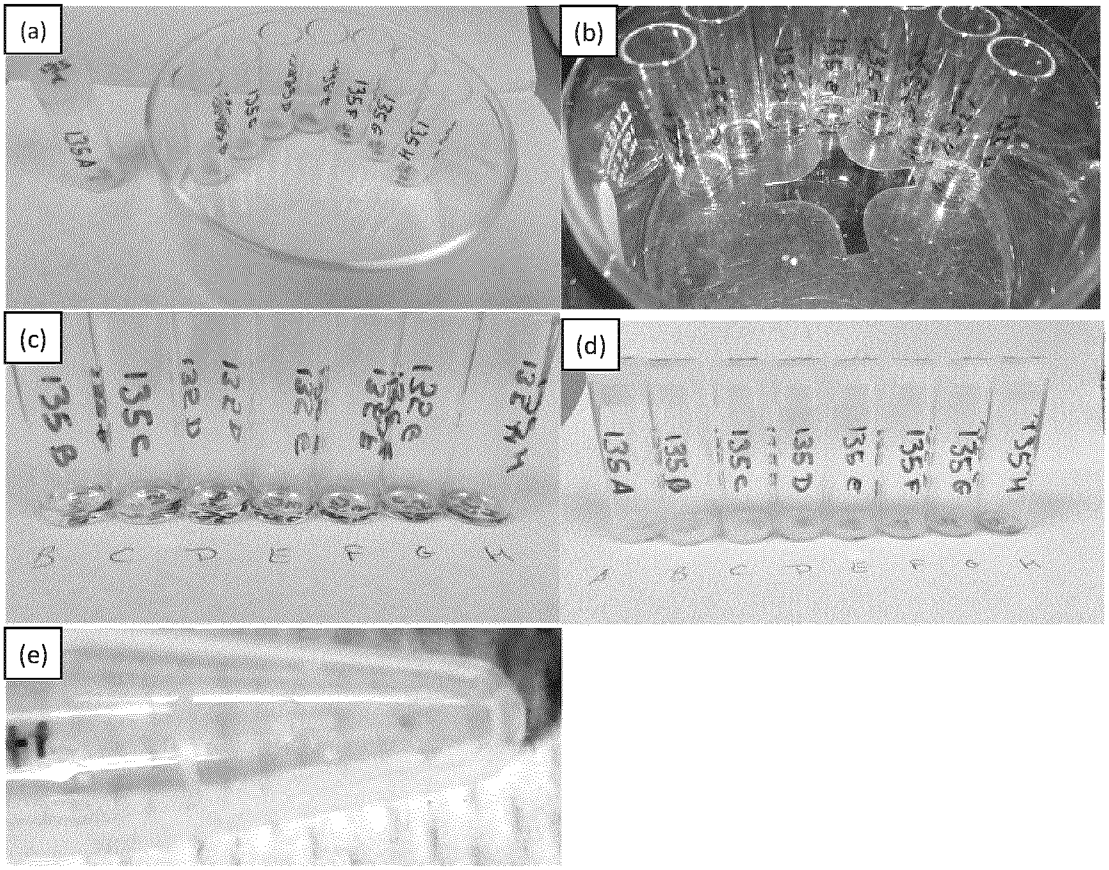
FIG. 7 is a series of photos of samples of cross-linked paraffin wax at various stages of the process: (a) after mixing, before cross-linking; (b) cross-linking in the oven at 110° C.; (c) after cross-linking, just out of the oven; (d) after cross-linking, cooled down to room temperature; (e)

With reference to FIG. 7, it can be seen that:

1. All samples placed in the oven melted.
2. The activation of crosslinker caused the doped samples t turn yellow, and more so with higher loadings.
3. When allowed to cool down to room temperature, all samples returned to opaque solids, with a yellow coloration increasing with the crosslinker loading.
4. Sample H, loaded with 200 w % CL-HF2PH was only partially soluble and produced a swollen, insoluble fraction.

GPC analysis of the dissolved samples (see FIG. 8) shows several key features supporting the crosslinking mechanism at play:

1. Decrease of the nominal molecular weight species with increasing loadings of crosslinker.
2. Increase of higher molecular weight species (with high dispersity) with increasing loadings of crosslinker.
3. Increase of fraction of CL-HF2PH bound to the nominal molecular weight species with increasing loadings of crosslinker.
4. Increase of fraction of CL-HF2PH bound to the higher molecular weight species with increasing loadings of crosslinker.

GPC analysis also confirms insolubility of sample H (loaded with 200 w % CL-HF2PH), as the intensity of the signal is significantly lower in all three channels (see FIG. 8, dashed lines).

Example 19: Strengthening of UHMWPE Fabric

Material used: two grades of fabric made of woven fibers of ultra-high molecular weight polyethylene (UHMWPE), characterized by their area density: 75 g/$m^2$ and 90 g/$m^2$.

Procedure: the fabric was impregnated with CL-HF2PH by placing a piece of desired dimensions into a close-fitting aluminum pan filled with a solution of the crosslinker in pentane at the appropriate concentration. This concentration was calculated to impregnate the fabric with 1 w % or 10 w % of crosslinker, but in order to compensate for crosslinker deposited on the sides and bottom of the aluminum pan, an extra 0.25 w % and 2.5 w % (resp.) was added: for a given piece of fabric, the amount of crosslinker in the solution was 1.25 w % or 12.5 w % (resp.) of its mass. For instance, a 10 cm×10 cm piece of 75 g/$m^2$ fabric (weight=750 mg) was impregnated using a solution containing 93.7 mg (12.5 w %) crosslinker, in order to provide a 10 w %-impregnated sheet. The bath was covered with aluminum foil and left to sit at room temperature for 1 h. Then the cover was removed to allow the pentane to evaporate in a well-ventilated fume hood, generally within 20 min. After evaporation, the impregnated sheets of fabric were wrapped in aluminum foil and placed in an oven at 110° C. for 4 h. If not covered by aluminum, it was noticed that the crosslinker could evaporate (loss of the impregnated mass) before reacting at high temperature, most likely due to increased surface exposure.

To study the impact of the pentane bath and oven baking, "vehicle control" samples were prepared following the same procedure, but without adding crosslinker in the pentane bath.

To distinguish the impact of added weight versus actual crosslinking, a set of "molecular control" samples (based on the 90 g/$m^2$ fabric) was prepared following the same procedure but where the crosslinker was replaced by an analogous structure (MC-HF2PH, see below) bearing only one diazirine moiety (and therefore incapable of crosslinking).

MC-HF2PH

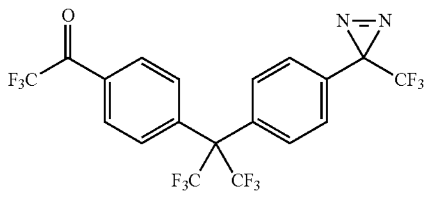

Chemical Formula: $C_{19}H_8F_{12}N_2O$
Molecular Weight: 508.27

Following the treatment, the mechanical and morphological properties of the samples were analyzed using various techniques. One representative example, namely tear testing data of 10 cm×10 cm squares of treated fabric, is shown in FIG. 9.

General observations and conclusions: fabric treated with crosslinker was stiffer than the rest of samples, and more so with the 10 w %. The tear-strength measured for samples treated with CL-HF2PH (at both 1% and 10% loadings)—but not for samples treated with MC-HF2PH—greatly increased. These data confirm the expected increase in material strength following crosslinking.

There is incorporated by reference published Science paper, "A Broadly Applicable Crosslinker for Aliphatic Polymers Containing C—H bonds", M. L. Lepage, C. Simhadri, C. Liu, M Takaffoli, L. Bi., B. Crawford, A. S. Milani, J. E. Wulff, Science, 2019, 366,-875.

This science paper provides further examples that support the utility of the present invention.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

The scope of the claims should not be limited by the illustrated embodiments set forth as examples, but should be given the broadest interpretation consistent with a purposive construction of the claims in view of the description as a whole.

What is claimed is:

1. A compound of Formula I:

Formula I

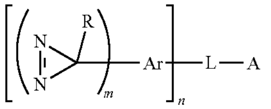

wherein:

R, in each instance, is independently selected from the group consisting of halogenated alkyl having 1 to 6 carbons and halogenated cycloalkyl having 1 to 6 carbons;

L is a linker moiety selected from the group consisting of null, halogenated alkylene having 1 to 12 carbons;

A is absent; and wherein:

when Ar is a heteroaromatic group, then L is null, m is 2 and n is 1;

or when Ar is null, then L is a halogenated alkylene group having 1 to 12 carbons, m is 1 and n is 2.

2. The compound of claim 1, selected from the group consisting of: 3,3'-((perfluoropropane-2,2-diyl)bis(4,1-phenylene))bis(3-(trifluoromethyl)-3H-diazirine), 3,3'-((perfluorooctane-1,8-diyl)bis(4,1-phenylene))bis(3-(trifluoromethyl)-3H-diazirine), 3,3'-(perfluorooctane-1,8-diyl)bis(3-(trifluoromethyl)-3H-diazirine), 3,3'-((perfluorooctane-1,8-diyl)bis(2,3,5,6-tetrafluoro-4,1-phenylene))bis(3-(trifluoromethyl)-3H-diazirine), and 3,3'-(perfluorooctane-1,8-diyl) bis(3-(trifluoromethyl)-3H-diazirine).

* * * * *